United States Patent
Newell et al.

(10) Patent No.: US 8,557,764 B2
(45) Date of Patent: Oct. 15, 2013

(54) METHODS OF MODULATING IMMUNE FUNCTION

(75) Inventors: Martha Karen Newell, Colorado Springs, CO (US); Evan Newell, Menlo Park, CA (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 308 days.

(21) Appl. No.: 12/011,643

(22) Filed: Jan. 28, 2008

(65) Prior Publication Data

US 2009/0258027 A1  Oct. 15, 2009

Related U.S. Application Data

(60) Provisional application No. 60/886,852, filed on Jan. 26, 2007, provisional application No. 60/906,731, filed on Mar. 13, 2007.

(51) Int. Cl.
*A61K 38/08* (2006.01)

(52) U.S. Cl.
USPC .......................................................... 514/3.8

(58) Field of Classification Search
None
See application file for complete search history.

(56) References Cited

U.S. PATENT DOCUMENTS

| | | |
|---|---|---|
| 5,616,554 A | 4/1997 | Beardsley |
| 5,756,666 A | 5/1998 | Takiguchi et al. |
| 6,165,493 A | 12/2000 | Neurath et al. |
| 6,245,904 B1 | 6/2001 | Melms et al. |
| 6,326,465 B1 | 12/2001 | Hess |
| 7,252,829 B1 | 8/2007 | Sette et al. |
| 7,276,478 B2 | 10/2007 | Sivakumar et al. |
| 7,312,318 B2 | 12/2007 | Hansen et al. |
| 2002/0164685 A1 | 11/2002 | Rosen et al. |
| 2002/0182222 A1 | 12/2002 | Groot |
| 2002/0187526 A1 | 12/2002 | Ruben et al. |
| 2003/0138433 A1 | 7/2003 | Newell et al. |
| 2004/0018639 A1* | 1/2004 | Zhabilov et al. ............ 436/518 |
| 2005/0048055 A1 | 3/2005 | Newell et al. |
| 2005/0048071 A1 | 3/2005 | Bae et al. |
| 2005/0196385 A1 | 9/2005 | Romagne et al. |
| 2005/0271676 A1 | 12/2005 | Sette et al. |
| 2006/0008448 A1 | 1/2006 | Xu et al. |
| 2006/0057123 A1 | 3/2006 | Ettinger et al. |
| 2007/0071770 A1 | 3/2007 | Sutter et al. |
| 2008/0057039 A1 | 3/2008 | Newell et al. |
| 2008/0095798 A1 | 4/2008 | Humphreys et al. |
| 2009/0175838 A1 | 7/2009 | Newell et al. |
| 2010/0034839 A1 | 2/2010 | Newell et al. |
| 2010/0166782 A1 | 7/2010 | Newell et al. |
| 2010/0166789 A1 | 7/2010 | Keledjian et al. |
| 2011/0118175 A1* | 5/2011 | Newell et al. ................ 514/3.7 |

FOREIGN PATENT DOCUMENTS

| | | |
|---|---|---|
| CN | 1 458 165 A | 11/2003 |
| EP | 332865 A2 | 9/1989 |
| EP | 0524796 A1 | 1/1993 |
| WO | WO 97/25344 A1 | 7/1997 |
| WO | WO 98/18491 A1 | 5/1998 |
| WO | WO 00/39283 A1 | 7/2000 |
| WO | WO 00/78348 A1 | 12/2000 |
| WO | WO 03/031643 A2 | 4/2003 |
| WO | WO 2004/043361 A2 | 5/2004 |
| WO | WO 2004/047719 A2 | 6/2004 |
| WO | WO 2005/079523 A2 | 9/2005 |
| WO | WO 2006/118821 A2 | 11/2006 |
| WO | WO 2008/054635 A2 | 5/2008 |

OTHER PUBLICATIONS

O'Brien et al., Immunol Rev. Feb. 2007;215:77-88.*
Nanno et al., Immunol Rev. Feb. 2007;215:103-13.*
Lederman et al., J Infect Dis. Dec. 15, 2006;194(12):1677-85.*
Mamikonyan et al., Current HIV Research, 2008, 6, 318-326.*
Alter et al., Current Molecular Medicine 2006, 6, 621-629.*
Montoya et al., Clinical Immunology (2006) 120, 138-146.*
Schindler et al., AIDS 2007, 21:1103-1107.*
Valentin et al., Virology 269, 294-304 (2000).*
Savarino et al., Journal of Clinical Virology 20 (2001) 131-135.*
Nowell et al., J Exp Med. Oct. 1, 1985;162(4):1371-6.*
Adams et al., Biological activity and therapeutic potential of homologs of an Ii peptide which regulates antigenic peptide binding to cell surface MHC class II molecules. Arzneimittelforschung. Sep. 1997;47(9):1069-77.
Ayala-Gaytan et al., Diminution of plasma viral load and cultured HIV-infected peripheral blood mononuclear cells in non-responding patients treated with two calf thymus nuclear proteins and conventional antiretrovirals. HIV AIDS Rev. 2004;3(3):8-13.
Badger et al., Comparative genomic evidence for a close relationship between the dimorphic prosthecate bacteria *Hyphomonas neptunium* and *Caulobacter crescentus*. J Bacteriol. Oct. 2006;188(19):6841-50.
Barrera et al., The role of the invariant chain in mucosal immunity. Int Arch Allergy Immunol. Oct. 1998;117(2):85-93.
Bhushan et al., Drug resistance results in alterations in expression of immune recognition molecules and failure to express Fas (CD95). Immunol Cell Biol. Aug. 1998;76(4):350-6.
Bielekova et al., Regulatory D56(bright) natural killer cells mediate immunomodulatory effects of IL-2Ralpha-targeted therapy (daclizumab) in multiple sclerosis. Proc Natl Acad Sci U S A. Apr. 11, 2006;103(15):5941-6. Epub Apr. 3, 2006.
Burrows et al., A murine model for antibody-directed targeting of vascular endothelial cells in solid tumors. Cancer Res. Nov. 1, 1992;52(21):5954-62.
Cambier et al., Coupling of B cell surface Ig, Ia and BSF1 receptors to intracellular "second messengers". Adv Exp Med Biol. 1987;213:195-205.

(Continued)

*Primary Examiner* — Zachary Skelding
(74) *Attorney, Agent, or Firm* — Wolf, Greenfield & Sacks, P.C.

(57) ABSTRACT

The invention relates to methods for modulating the immune function through targeting of CLIP molecules as well as gamma delta T cells. The result is wide range of new therapeutic regimens for treating, inhibiting the development of, or otherwise dealing with, a multitude of illnesses and conditions, including autoimmune disease, transplant and cell graft rejection, cancer, bacterial infection, HIV infection, and AIDS, as well as novel methods of diagnosis and of introducing a treatment regimen into a subject.

7 Claims, 8 Drawing Sheets

(56) References Cited

OTHER PUBLICATIONS

Cambier et al., Differential transmembrane signaling in B lymphocyte activation. Ann N Y Acad Sci. 1987;494:52-64.
Cambier et al., Transmembrane signals and intracellular "second messengers" in the regulation of quiescent B-lymphocyte activation. Immunol Rev. Feb. 1987;95:37-57.
Cantin et al., A novel virus capture assay reveals a differential acquisition of host HLA-DR by clinical isolates of human immunodeficiency virus type 1 expanded in primary human cells depending on the nature of producing cells and the donor source. J Gen Virol. Dec. 2001;82(Pt 12):2979-87.
Castellino et al., Antigen presentation by MHC class II molecules: invariant chain function, protein trafficking, and the molecular basis of diverse determinant capture. Hum Immunol. May 1997;54(2):159-69.
Chaturvedi et al., The functional role of class II-associated invariant chain peptide (CLIP) in its ability to variably modulate immune responses. Int Immunol. Jun. 2000;12(6):757-65.
Cheng, A novel immunotherapeutic for cancer and autoimmune diseases. Drug Disc Devel. Feb. 22, 2012. Last accessed online via http://www.dddmag.com/articles/2012/02/novel-immunotherapeutic-cancer-and-autoimm . . . on Nov. 19, 2012. 5 pages.
Conner, Systemic lupus erythematosus; a report on twelve cases treated with quinacrine (atabrine) and chloroquine (aralen). Ann Rheum Dis. Mar. 1957;16(1):76-81.
Desbarats et al., Dichotomy between naïve and memory CD4(+) T cell responses to Fas engagement. Proc Natl Acad Sci U S A. Jul. 6, 1999;96(14):8104-9.
Desbarats et al., Fas (CD95) expression and death-mediating function are induced by CD4 cross-linking on CD4+ T cells. Proc Natl Acad Sci U S A. Oct. 1, 1996;93(20):11014-8.
Desbarats et al., Fas engagement induces neurite growth through ERK activation and p35 upregulation. Nat Cell Biol. Feb. 2003;5(2):118-25.
Desbarats et al., Newly discovered role for Fas ligand in the cell-cycle arrest of CD4+ T cells. Nat Med. Dec. 1998;4(12):1377-82.
Desbarats et al., Rapid early onset lymphocyte cell death in mice resistant, but not susceptible to *Leishmania* major infection. Apoptosis. Apr. 2000;5(2):189-96.
Dorrell et al., Cytotoxic T lymphocytes recognize structurally diverse, clade-specific and cross-reactive peptides in human immunodeficiency virus type-1 gag through HLA-B53. Eur J Immunol. Jun. 2001;31(6):1747-56.
Folzenlogen et al., Analysis of CD80 and CD86 expression on peripheral blood B lymphocytes reveals increased expression of CD86 in lupus patients. Clin Immunol Immunopathol. Jun. 1997;83(3):199-204.
Frölich et al., The anti-CD74 humanized monoclonal antibody, milatuzumab, which targets the invariant chain of MHC II complexes, alters B-cell proliferation, migration, and adhesion molecule expression. Arthritis Res Ther. Mar 9, 2012;14(2):R54. doi: 10.1186/ar3767.
Fuld et al., Treatment of rheumatoid arthritis with chloroquine. Br Med J. Nov. 15, 1958;2(5106):1199-201.
Ghittoni et al., Simvastatin inhibits the MHC class II pathway of antigen presentation by impairing Ras superfamily GTPases. Eur J Immunol. Nov. 2006;36(11):2885-93.
Gunther et al., Bidirectional binding of invariant chain peptides to an MHC class II molecule. Proc Natl Acad Sci U S A. Dec. 21, 2010;107(51):22219-24. Epub Nov. 29, 2010.
Heinonen et al., T-cell protein tyrosine phosphatase deletion results in progressive systemic inflammatory disease. Blood. May 1, 2004;103(9):3457-64. Epub Jan. 15, 2004.
Hillman et al., Generating MHC Class II+/Ii- phenotype after adenoviral delivery of both an expressible gene for MHC Class II inducer and an antisense Ii-RNA construct in tumor cells. Gene Ther. Aug. 2003;10(17):1512-8.
Hitzel et al., The invariant chain derived fragment CLIP is an efficient in vitro inhibitor of peptide binding to MHC class II molecules. Mol Immunol. Jan. 1996;33(1):25-31.

Huber et al., Apoptosis in coxsackievirus B3-induced myocarditis and dilated cardiomyopathy. Ann N Y Acad Sci. 1999;887:181-90.
Huber et al., Estradiol prevents and testosterone promotes Fas-dependent apoptosis in CD4+ Th2 cells by altering Bcl 2 expression. Lupus. 1999;8(5):384-7.
Huber et al., gamma delta+ T cells regulate major histocompatibility complex class II(IA and IE)-dependent susceptibility to coxsackievirus B3-induced autoimmune myocarditis. J Virol. Jul. 1999;73(7):5630-6.
Huber et al., Hormonal regulation of CD4(+) T-cell responses in coxsackievirus B3-induced myocarditis in mice. J Virol. Jun. 1999;73(6):4689-95.
Huber et al., T helper-cell phenotype regulates atherosclerosis in mice under conditions of mild hypercholesterolemia. Circulation. May 29, 2001;103(21):2610-6.
Huber et al., V gamma 1+ T cells suppress and V gamma 4+ T cells promote susceptibility to coxsackievirus B3-induced myocarditis in mice. J Immunol. Oct. 15, 2000;165(8):4174-81.
Kalita et al., Computational modelling and simulation of the immune system. Int J Bioinform Res Appl. 2006;2(1):63-88.
Kang et al., Low-dose peptide tolerance therapy of lupus generates plasmacytoid dendritic cells that cause expansion of autoantigen-specific regulatory T cells and contraction of inflammatory Th17 cells. J Immunol. Jun. 15, 2007;178(12):7849-58.
Kasai et al., CLIP-derived self peptides bound to MHC class II molecules of medullary thymic epithelial cells differ from those of cortical thymic epithelial cells in their diversity, length, and C-terminal processing. Eur J Immunol. Dec. 2000;30(12):3542-51.
Katada et al., B cell-B cell interaction through intercellular adhesion molecule-1 and lymphocyte functional antigen-1 regulates immunoglobulin E synthesis by Bcells stimulated with interleukin-4 and anti-CD40 antibody. Eur J Immunol. Jan. 1996;26(1):192-200.
LaMarre et al., Class II MHC molecules and the HIV gp 120 envelope protein interact with functionally distinct regions of the CD4 molecule. EMBO J. Nov. 1989;8(11):3271-7.
Lang et al., Toll-like receptor engagement converts T-cell autoreactivity into overt autoimmune disease. Nat Med. Feb. 2005;11(2):138-45. Epub Jan. 16, 2005.
Lederman et al., Cyclosporin A provides no sustained immunologic benefit to persons with chronic HIV-1 infection starting suppressive antiretroviral therapy: results of a randomized, controlled trial of the AIDS Clinical Trials Group A5138. J Infect Dis. Dec. 15, 2006;194(12):1677-85. Epub Nov. 2, 2006.
Lu et al., Suppression of major histocompatibility complex class II-associated invariant chain enhances the potency of an HIV gp120 DNA vaccine. Immunology. Feb. 2007;120(2):207-16. Epub Nov. 20, 2006.
Matza et al., Invariant chain, a chain of command. Trends Immunol. May 2003;24(5):264-8.
Mozes et al., A novel synthetic peptide for the specific treatment of lupus: clinical effects and mechanism of action. Isr Med Assoc J. Jan. 2008;10(1):40-2.
Newell et al., Biochemical characterization of proteins that co-purify with class II antigens of the murine MHC. J Immunol. Mar. 15, 1988;140(6):1930-8.
Newell et al., Cellular metabolism as a basis for immune privilege. J Immune Based Ther. Vaccines. Mar. 17, 2006;4:1.
Newell et al., Death of mature T cells by separate ligation of CD4 and the T-cell receptor for antigen. Nature. Sep. 20, 1990;347(6290):286-9.
Newell et al., Ligation of major histocompatibility complex class II molecules mediates apoptotic cell death in resting B lymphocytes. Proc Natl Acad Sci U S A. Nov. 15, 1993;90(22):10459-63.
Newell et al., The effects of chemotherapeutics on cellular metabolism and cosequent immune recognition. J Immune Based Ther Vaccines. Feb. 2, 2004;2(1):3.
Newell et al., TLR-mediated B cell activation results in ectopic CLIP expression that promotes B cell-dependent inflammation. J Leukoc Biol. Oct. 2010;88(4):779-89. Epub Jul. 14, 2010.
Newell, Transmembrane signaling through major histocompatability complex (MCH) encoded molecules, 1987, University of Colorado Health Services Center, Denver, CO.

(56) References Cited

OTHER PUBLICATIONS

Newell et al., Fas ligand: receptor or ligand? Apoptosis. Oct. 1999;4(5):311-5.
Noveljic et al., Virological responses of treatment-naïve stage CDC-2 HIV-1 positive subjects receiving VGV-1 injections in a blinded, placebo-controlled, multi-centre clinical trial. Retrovirology. 2006;3(Suppl 1): P73.
O'Brien et al., gammadelta T-cell receptors: functional correlations. Immunol Rev. Feb. 2007;215:77-88.
Ohba et al., Evolutionary relationship of hepatitis C, pesti-, flavi-, plantviruses, and newly discovered GB hepatitis agents. FEBS Lett. Jan. 5, 1996;378(3):232-4.
Paulsen et al., Antimicrobial peptides are expressed and produced in healthy and inflamed human synovial membranes. J Pathol. Nov. 2002;198(3):369-77.
Peter et al., The CD95 receptor: apoptosis revisited. Cell. May 4, 2007;129(3):447-50.
Powis, CLIP-region mediated interaction of Invariant chain with MHC class I molecules. FEBS Lett. May 29, 2006;580(13):3112-6. Epub Apr. 27, 2006.
Roberts et al., Host protein incorporation is conserved among diverse HIV-1 subtypes. AIDS. Feb. 25, 1999;13(3):425-7.
Röhn et al., Upregulation of the CLIP self peptide on mature dendritic cells antagonizes T helper type 1 polarization. Nat Immunol. Sep. 2004;5(9):909-18.
Schindler et al., Down-modulation of mature major histocompatibility complex class II and up-regulation of invariant chain cell surface expression are well-conserved functions of human and simian immunodeficiency virus nef alleles. J Virol. Oct. 2003;77(19):10548-56.
Schweitzer et al., Endogenous versus exogenous fatty acid availability affects lysosomal acidity and MHC class II expression. J Lipid Res. Nov. 2006;47(11):2525-37. Epub Aug. 16, 2006.
Snell et al, The Nobel Lectures in Immunology. Lecture for the Nobel Prize for Physiology or Medicine. Studies in histocompatibility, Scand J Immunol. Oct.; 36(4):513-26 (1992).
Stein et al., CD74: a new candidate target for the immunotherapy of B-cell neoplasms. Clin Cancer Res. Sep. 15, 2007;13(18 Pt 2):5556s-5563s.
Stumptner et al., Interaction of MHC class II molecules with the invariant chain: role of the invariant chain (81-90) region. EMBO J. Oct. 1, 1997;16(19):5807-18.
Stumptner-Cuvelette et al., HIV-1 Nef impairs MHC class II antigen presentation and surface expression. Proc Natl Acad Sci U S A. Oct. 9, 2001;98(21):12144-9. Epub Oct. 2, 2001.
Tian et al., Attenuation of inducible Th2 immunity with autoimmune disease progression. J Immunol. Nov. 15, 1998;161(10):5399-403.
Truman et al., HLA class II signaling mediates cellular activation and programmed cell death. Exp Hematol. Oct. 1996;24(12):1409-15.
Truman et al., HLA class II-mediated death is induced via Fas/Fas ligand interactions in human splenic B lymphocytes. Blood. Mar. 15, 1997;89(6):1996-2007.
Wagner et al., Increased expression of CD40 on thymocytes and peripheral T cells in autoimmunity: a mechanism for acquiring changes in the peripheral T cell receptor repertoire. Int J Mol Med. Sep. 1999;4(3):231-42.
Wagner et al., Rescue of thymocytes from glucocorticoid-induced cell death mediated by CD28/CTLA-4 costimulatory interactions with B7-1/B7-2. J Exp Med. Nov. 1, 1996;184(5):1631-8.
Wu et al., The MHC class II-associated invariant chain-derived peptide clip binds to the peptide-binding groove of class II molecules. Mol Immunol. Mar.-Apr. 1996;33(4-5):371-7.
Xu et al., Immunotherapy of cancer by antisense inhibition of Ii protein, an immunoregulator of antigen selection by MHC class II molecules. Curr Opin Mol Ther. Apr. 2004;6(2):160-5.
Zhao et al., Acute and relapsing experimental autoimmune encephalomyelitis in IL-4- and alpha/beta T cell-deficient C57BL/6 mice. J Neuroimmunol. Jul. 1, 1998;87(1-2):171-8.

* cited by examiner

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Met Arg Met Ala Thr Pro Leu Leu Met
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 2

Phe Arg Ile Met Ala Val Leu Ala Ser
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 3

Pro Lys Tyr Val Lys Gln Asn Thr Leu Lys Leu Ala Thr
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 4

Ile Ala Gly Phe Lys Gly Glu Gln Gly Pro Lys Gly Glu
1               5                   10

<210> SEQ ID NO 5
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 5

Ser Gly Gly Gly Ser Lys Met Arg Met Ala Thr Pro Leu Leu Met Gln
1               5                   10                  15

Ala Leu Tyr
```

METHODS OF MODULATING IMMUNE FUNCTION

RELATED APPLICATION

This application claims priority under 35 USC §119 to U.S. Provisional Application No. 60/886,852, filed Jan. 26, 2008, and U.S. Provisional Application No. 60/906,731, filed Mar. 13, 2007, the entire contents of which is hereby incorporated by reference.

BACKGROUND OF INVENTION

Major Histocompatiblity Complex (MHC)-encoded molecules are key components of T cell immunity. The significance of these molecules as tissue compatibility molecules was first observed in the late 1930s. Peter Gorer and George Snell observed that when tumors were transplanted from a genetically non-identical member of the same species, the tumors were always rejected, but when tumors were transplanted between genetically identical members of the same species, the tumor would "take" and would grow in the syngeneic animal. The genetic complex responsible for the rejection was subsequently found to be a series of genes that encode protein products known as Major Histocompatibility molecules. These genes, also known as immune response or IR genes, and their protein products are responsible for all graft rejection. There are two types of MHC molecules: MHC class I and MHC class II. All nucleated cells express cell surface MHC class I. A subset of specialized cells express class II MHC. Included in the specialized, professional antigen-presenting cells (APCs) are B cells, macrophages, microglia, dendritic cells, and Langerhans cells among others.

As stated above, B cells express MHC class II. Once antigen has been bound by the antigen receptor on the B cell, the antigen and its receptor are engulfed into an endosomal compartment. This compartment fuses with another compartment known as the lysosome. The B cell is very efficient at breaking down antigens into smaller parts and loading the parts into MHC class II in the lysosome. The MHC is then trafficked to the cell surface where the B cell can effectively "show" the antigen to a CD4+ T cell. The activated CD4 cell is also called a helper cell and there are two major categories, Th1 and Th2.

The MHC molecules are tightly protected in the endosomal/lysosomal compartments to insure that only antigens for which we need a response get presented to T cells. MHC class II molecules, prior to antigen loading, are associated with a molecule called invariant chain, also known as CD74. The invariant chain is associated with MHC class II (and recently shown to be associated with certain MHC class I molecules) prior to antigen loading into the antigen binding grooves of the MHC molecules. As antigen is processed, the invariant chain gets cleaved by proteases within the compartment. First an end piece is removed, and then another known as CLIP (class II invariant chain associated peptide). CLIP fills the groove that will ultimately hold the antigen until the antigen is properly processed. For a detailed review of the invariant chain, including CLIP, see Matza et al. (2003), incorporated herein in its entirety. Despite the fact that this "chaperone" role for invariant chain and CLIP has been identified, the full impact of these molecules on immune signaling and activation has yet to be determined.

The history of prodrug administration includes the use of esterases available throughout the digestive track in humans. The esterase acts as a hydrolase in ester hydrolysis, cleaving the carboxylate ester from the alcohol. The purpose of this approach has generally included the improvement of absorbtion, metabolism, and overall bioavailability. The application has been used in various drugs including, but not limited to, Enalapril, Valacyclovir, Heroin, and Chloramphenicol.

SUMMARY OF INVENTION

The invention is based at least in part on the discovery that inhibitors of γδT cell expansion, activation and/or effector function are useful in the treatment of disorders such as HIV infection, autoimmune disease and tissue graft rejection. The invention is also based on the discovery that the same disorders can be treated by inhibiting CLIP presentation in MHC on a cell surface.

The invention in some aspects is a method for treating a disorder associated with γδT cell expansion, activation and/or effector function by contacting a CLIP molecule expressing cell with an inhibitor of γδT cell expansion, activation and/or effector function in an effective amount to interfere with γδT cell expansion, activation and/or effector function by the CLIP molecule expressing cell. In some embodiments the γδT cell is a vγ9vδ2 T cell. Disorders associated with γδT cell expansion and/or activation include, for instance autoimmune disease, HIV infection, and cell, tissue and graft rejection.

The CLIP molecule expressing cell is a B cell in some embodiments. In other embodiments the CLIP compound expressing cell is a neuron, an oligodendrocyte, a microglial cell, or an astrocyte. In yet other embodiments the CLIP compound expressing cell is a heart cell, a pancreatic beta cell, an intestinal epithelial cell, a lung cell, an epithelial cell lining the uterine wall, and a skin cell. When the cell is a B cell, the method may further involve contacting the B cell with an anti-HLA class I or II antibody in an effective amount to kill the B cell.

In another aspect the invention is a method for treating a subject having autoimmune disease by administering to the subject a CLIP inhibitor in an effective amount to reduce CLIP function in a CLIP molecule expressing cell of the subject. In some embodiments the autoimmune disease is multiple sclerosis, systemic lupus erythematosus, type 1 diabetes, viral endocarditis, viral myocarditis, viral encephalitis, rheumatoid arthritis, Graves' disease, autoimmune thyroiditis, autoimmune myositis, discoid lupus erythematosus, Crohns disease, Sjogren's syndrome, Reiter's syndrome, Rheumatoid arthritis, Lyme Disease, myasthenia gravis, Kawasaki's disease, Celiac disease, Goodpasture's syndrome, or aplastic anemia.

A method for treating a subject infected with HIV by administering to the subject a CLIP inhibitor in an effective amount to reduce CLIP function in a CLIP molecule expressing cell of the subject is provided according to other aspects of the invention. Optionally, the method further involves removing antigen non-specifically activated B cells and/or γδT cells from the subject.

In yet another aspect the invention is a method for treating a subject having a cell or tissue graft, by administering to the subject a CLIP inhibitor in an effective amount to reduce CLIP function in the cell or tissue graft, or hematopoeitic cells in the tissue graft, in order to inhibit cell or tissue graft rejection in the subject. In some embodiments the graft tissue or cell is heart, lung, kidney, skin, cornea, liver, neuronal tissue or cell, stem cell, including hematopoetic or embryonic stem cell.

In some embodiments the CLIP molecule is CLIP. In other embodiments the CLIP molecule is CD74.

The inhibitor of γδT cell expansion, activation and/or effector function may be a CLIP expression inhibitor. CLIP expression inhibitors include, for instance, an siRNA of a CLIP molecule or HLA-DO as well as antisense molecules.

In other embodiments the inhibitor of γδT cell expansion, activation and/or effector function is a CLIP activity inhibitor. The CLIP activity inhibitor may be an agent that displaces CLIP. Agents that displace CLIP include but are not limited to chloroquine, a lysosomatropic agent, peptide/lipopeptide antigen, small molecular compound pCP, chlorobenzene (CB), and parachloroanisol (pCA), peptide HA306-318 (PKYVKQNTLKLAT) (SEQ ID NO. 3), or peptide CO260-272 (IAGFKGEQGPKGE) (SEQ ID NO. 4). In some embodiments the agent that displaces CLIP is FRIMAVLAS (SEQ ID NO. 2). In other embodiments the agent that displaces CLIP is an HLA binding peptide. In yet other embodiments the agent that displaces CLIP is a pharmacon that is a combination of a glycolytic inhibitor and a halogenated alky ester. Alternatively, the CLIP activity inhibitor is an anti-CLIP antibody or recombinant HLA-DM. In some embodiments the anti-CLIP antibody is specific for CLIP in the context of MHC class II. In other embodiments the anti-CLIP antibody is specific for CLIP in the context of MHC class I. In other embodiments the CLIP activity inhibitor is an agent that inhibits CD74 processing, such as cystatin A, B or C.

In some embodiments the method further includes exposing the CLIP molecule expressing cell to an MHC class I or II loading peptide.

In other aspects the invention is a method for treating a subject having a disorder associated with γδT cell expansion, activation and/or effector function by removing antigen non-specifically activated B cells and/or γδT cells from the subject to treat the disorder.

In yet another aspect the invention is a method for inducing B cell death, by inducing CLIP molecule expression on an antigen non-specifically activated B cell and contacting the antigen non-specifically activated B cell with an anti-HLA class II antibody in an effective amount to kill the antigen non-specifically activated B cell.

In some embodiments the B cell is in vitro. In other embodiments the B cell is in a subject. The subject may be administered a CLIP inducing agent. CLIP inducing agents include but are not limited to CLIP expression vectors and CLIP activators. The subject may have an autoimmune disease or be infected with HIV.

A method for displacing CLIP from the surface of a cell is provided according to other aspects of the invention. The method may be performed by administering a halogenated alky ester or as a pharmacon a combination of a glycolytic inhibitor and a halogenated alky ester to a subject to displace CLIP from the surface of the cell. In some embodiments the pharmacon is a single bifunctional compound acting as a prodrug.

In other embodiments the glycolytic inhibitor is a 2-deoxyglucose. Optionally, the 2-deoxyglucose is 2-deoxy-D-glucose. The halogenated alky ester may be, for instance, dichloroacetate or salts thereof.

A composition of a bifunctional compound of a glycolytic inhibitor and a halogenated alky ester is provided according to other aspects of the invention. In some embodiments the bifunctional compound has the following structure:

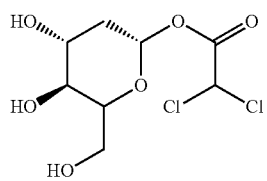

(2S,4R,5S)-4,5-dihydroxy-6-(hydroxymethyl)tetrahydro-2H-pyran-2-yl dichloroacetate In other embodiments the bifunctional compound has the following structure:

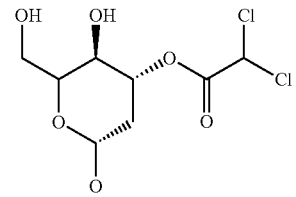

(3S,4R,6R)-3,6-dihydroxy-2-(hydroxymethyl)tetrahydro-2H-pyran-4-yl dichloroacetate In yet other embodiments the bifunctional compound has the following structure:

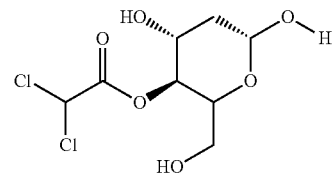

(3S,4R,6R)-4,6-dihydroxy-2-(hydroxymethyl)tetrahydro-2H-pyran-3-yl dichloroacetate The bifunctional compound may have the following structure:

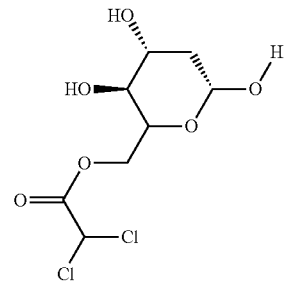

[(3S,4R,6R)-3,4,6-trihydroxytetrahydro-2H-pyran-2-yl]methyl dichloroacetate

The invention is also based on the findings that diseases such as cancer and infection by agents other than HIV can be treated by promoting CLIP on the surface such that γδT cells can cause the killing of the cancerous or infected cells. In other aspects of the invention a method for treating a subject having cancer by contacting a B-cell or cancer cell with a CLIP inducing agent in an effective amount to promote CLIP expression on the surface of the B-cell or cancer cell is provided.

In some embodiments the CLIP inducing agent is a CLIP expression vector. In other embodiments the CLIP inducing agent is a CLIP activator. The CLIP activator may be, for instance, nef or an agent that increases nef expression, ectopic CLIP, a palmitoylated protein or PAM, or an anti-CD40 or CD40L molecule in combination with IL-4. In some embodiments the CLIP activator is a HLA-DO molecule which promotes a higher HLA-DO:HLA-DM ratio. In yet other embodiments the CLIP activator is an anti-sense or siRNA to HLA-DM.

In some embodiments the cancer cell is a breast cancer cell, a lung cancer cell, a head & neck cancer cell, a brain cancer cell, an esophageal cancer cell, a liver cancer cell, a prostate cancer cell, a stomach cancer cell, an ovarian cancer cell, a uterine cancer cell, a cervical cancer cell, a testicular cancer cell, a skin cancer cell, a colon cancer cell, a leukemia cell, a lymphoma cell, a glioblastoma cell, a rhabdomyosarcoma cell, a melanoma cell, or a Kaposi's sarcoma cell. In some embodiments the cancer is primary, metastatic, recurrent or multi-drug resistant.

The methods may involve treating the subject with a standard anti-cancer therapy. Standard anti-cancer therapy includes for instance chemotherapy, radiotherapy or hormonal therapy.

A method of killing a cancer cell in a subject by (a) inducing cell surface expression of CLIP on a B cell; (b) contacting the B cell of step (a) with a γδT cell or NK cell and (c) contacting the γδT cell or NK cell with said cancer cell is provided according to other aspects of the invention. In some embodiments the step (a) is performed ex vivo and in other embodiments step (b) is performed in vivo.

In some embodiments the B cell of step (a) is allogeneic to the subject. In other embodiments the γδT cell of step (c) is allogeneic to the subject. In yet other embodiments the NK cell is allogeneic to the subject. In some embodiments the NK cell is a γδ+NK cell or NK T cells.

A method for treating a subject having a non-HIV infection by contacting a B-cell or a cell of the subject infected with a non-HIV infectious agent with a CLIP inducing agent in an effective amount to promote CLIP expression on the surface of the B-cell or the cell infected with a non-HIV infectious agent is provided according to other aspects of the invention.

In other aspects the invention is a method of activating a B cell, a macrophage or dendritic cell in an antigen non-specific fashion by inducing cell surface expression of CLIP in the cell. In some embodiments the cell is administered to a subject.

In some embodiments the activated cell is allogeneic to said subject. In other embodiments the activated cell is autologous to said subject. In yet other embodiments the cell is a B cell, a macrophage or dendritic cell.

A method of inhibiting activation of a cell selected from a γδT cell, an NK cell or an NK T cell in a subject by depleting antigen non-specifically activated B cells from said subject is provided according to other aspects of the invention. In one embodiment the depletion comprises leukophoresis. In other embodiments the depletion comprises antibody ablation. The subject may suffer from an autoimmune disease, HIV infection or be a transplant recipient. In some embodiments the γδT cell is a vγ9vδ2 T cell.

A method of providing an activated γδT cell to a subject by (a) obtaining a γδT cell; (b) contacting an antigen non-specifically activated B cell with said γδT cell; and (c) transferring said γδT cell once activated to said subject. In some embodiments the γδT cell is allogeneic to said subject. In other embodiments the γδT cell is autologous to said subject. In yet other embodiments the γδT cell is a vγ9vδ2 T cell.

In other aspects the invention is a method of diagnosing autoimmune disease or HIV infection comprising measuring levels of at least one defensin in a subject exhibiting one or more additional symptoms of autoimmune disease. In some embodiments the autoimmune disease is multiple sclerosis, systemic lupus erythematosus, type 1 diabetes, viral endocarditis, viral encephalitis, rheumatoid arthritis, Graves' disease, autoimmune thyroiditis, autoimmune myositis, discoid lupus erythematosus. In some embodiments the defensin is LL37.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3 depicts CLIP displacement from the surface of model B cells lines (Daudi and Raji) in response to thymic nuclear protein (TNP) mixture.

DETAILED DESCRIPTION

Figure 1:
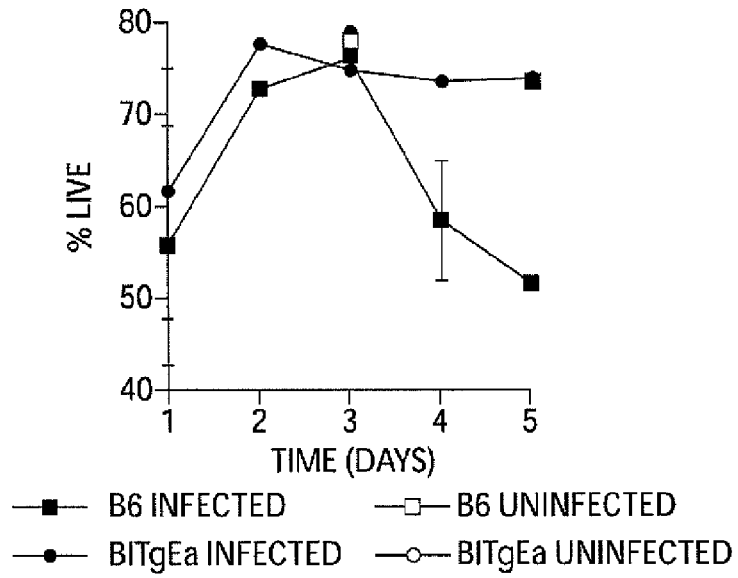
FIG. 1 depicts % B Cell Death in resistant C57B16 versus sensitive Coxsackievirus infected mice from 1 to 5 days post infection.

The present invention provides new insights into the role of invariant chain (CD74) and CLIP in disease and presents novel approaches to modulating the immune function through targeting of invariant chain/CD74 and CLIP. The result is wide range of new therapeutic regimens for treating or inhibiting the development or progression of a multitude of illnesses and conditions, including autoimmune disease, transplant and cell graft rejection, cancer, bacterial infection, HIV infection, as well as novel methods of diagnosis and of introducing a treatment regimen into a subject.

It has been discovered herein that B cells, in addition to producing antibodies, can also be activated in a somewhat antigen non-specific, bystander fashion. For example, during a viral or bacterial infection, non-antigen specific B cells in the area of the antigen-specific B cell that were in close proximity to an inflammatory or inciting lesion could manage to become activated in a bystander fashion. In those cases, CLIP would remain in the groove and get transported to the cell surface of the B cell. Its presence on the cell surface is dangerous because if CLIP gets plucked out of the groove by a self antigen, the B cell would be in a position to present self antigens to self-reactive T cells, a process that could lead to autoreactivity and autoimmune disease. For some B cells this may result in death to the B cell by a nearby killer cell, perhaps a natural killer (NK) cell. However, if this doesn't remove the potentially autoreactive B cell and it encounters a CD4+ T cell that can recognize that antigen (most likely one that was not in the thymus) the CLIP might be removed, in which case the B cell might receive additional help from a T cell specific for the antigen that now begins to occupy the groove (antigen binding location in the MHC molecule). Alternatively, a nearby cell whose job it is to detect damaged self cells, may become activated by the self antigen-presenting B cell. Such a damage detecting cell is, for example, a gamma delta-cell, also referred to as a γδT cell (γδ refers to the chains of its receptor), which can then seek out other sites of inflammation (for example in the brain in MS, in the heart for autoimmune myocarditis, in the pancreas in the case of Type I Diabetes). Alternatively, the γδT cell might attempt to kill the CD4 T cell that may respond to self antigens. In either event, activation of a γδT cell could be bad.

An example of the necessity for selective B cell death when the antigen receptor has not been bound by a real bona fide antigen is in Coxsackievirus. Most people that contract Coxsackievirus get a flu-like disease and then they recover, but in a genetic manner, some people (especially young men) contract Coxsackievirus and then go on to develop autoimmune myocarditis. In some genetically inbred strains of mice, the mice are resistant to myocarditis post-infection; in other strains of mice, the mice succumb. One difference was that the mice that were susceptible had a particular isoform of MHC class II. Mice on the resistant background having the other isoform of class II inserted, both artificially and genetically, showed susceptibility simply on the basis of the isoform, and it was shown that susceptibility depended on the presence of γδT cells (Huber et al., 1999).

Moreover, it was observed that in the mice that did not develop autoimmune disease, during the course of infection, all of their B cells died. Even with such B cell death, the animals survive as new B cells are produced continually. However, the animals susceptible to autoimmune disease had no B cell death. Further support for this notion is the γδ knock-out mice (they genetically have no γδT cells) do not get EAE, the mouse version of multiple sclerosis, nor do they get Type 1 diabetes. NK cell knock-out animals get worse disease in both cases. In addition, the invariant chain knock-out animals are resistant to the animal models of autoimmune diseases as well. Although not bound by mechanism, it is believed according to the invention that removal of γδT cells is a therapeutic treatment for MS, and that NK cells kill the antigen non-specific B cells in normal people and animals, thereby preventing disease. There appears to be a reciprocity of function between these two regulatory cell types.

Many therapies to block autoimmune and transplant disease involve eliminating or inhibiting B cells. No one knows the mechanism by which these B cell depleting therapies make people better. The inventor has observed that γδT cell activation is often associated with proteins that have been lipid modified. It turns out the invariant chain is fatty acid acylated (e.g., palmitoylated). As described in the examples below, antigen non-specifically activated human B cells were treated with anti-CLIP antibodies and subjected to flow cytometry. It was surprisingly found that these antigen-non-specifically activated B cells express cell surface CLIP. Thus, the inventor recognized that B cell surface expression of CLIP is likely how γδT cells get activated. For example, if there is inflammation at a given site, the long-lived γδT cell kills the type of CD4 helper T cell that could improve disease (the Th2 CD4+ T cells; these likely also express CLIP on their surfaces, making them a target for γδT cells), at the site of injury. They attack the inflamed tissue as well as kill the Th2 cells, leaving behind B cells that can now present self antigens (that load the CLIP binding site) to Th1 cells. The Th1 cells go on to activate additional CD8 killer cells and to attack the tissues as well. Once the γδT cell is activated, it searches for damaged tissue. Importantly, CLIP can preferentially associate with certain isoforms of MHC class II (I-E in mouse, HLA-DR in humans) and to certain MHC class I's (for example, but not limited to, CD1). Interestingly, many autoimmune diseases map to the same HLA-DR alleles and not to the other isoforms.

The invention, thus, involves treatments for autoimmune disease, transplantation, and infectious disease. In a particular example, during HIV infection, the AIDS virus encodes and induces expression of the HIV pathogenic factor, the nef gene product. This factor is known to increase viral replication in HIV infection. In addition the nef gene product down regulates the surface expression of MHC molecules while upregulating the cell surface expression of CD74. The nef gene product appears to selectively increase the cell surface expression of CLIP and CD74. If the ectopic/cell surface expression of Ii chain or its products is centrally important in activating γδT cells, the nef gene could promote activation of γδT cells that kill traditional HIV-affected CD4 T cells and the activation of NK cells that may promote viral replication or syncytia formation. Hence, it is distinctly possible that the killer of the CD4 T cells in AIDS are γδT cells. AIDS is characterized by an early bout of polyclonal B cell activation and symptoms of autoimmune disease, followed by the slow loss of T cells in waves. These particular γδT cells secrete an anti-biotic like protein called defensins, specifically one produced by the γδT cells in MS, known as LL-37. It is a protein that can be detected in the serum of people with activated γδT cells—this could be important as a diagnostic tool for a variety of diseases, including Multiple Sclerosis, other autoimmune diseases, as well as HIV disease.

Nef is a pathogenicity factor for HIV-1 infection. Expression of the gene is known to increase viral replication. CD4 T cells are important targets of HIV infection. Expression of the nef gene has been shown to down-regulate the level of CD4 and MHC class I on T cells, while increasing the level of expression of MHC class II CD74. In some experiments, researchers have shown a decrease in cell surface expression of mature major histocompatibility complex class II (MHC-II) molecules, while demonstrating an up-regulation of surface expression of the invariant chain (Ii) associated with immature MHC-II (Stumptner-Cuvelette et al., 2001). Furthermore, the investigators identified acidic residues, located at the base of the flexible C-proximal loop of Nef, that are critical for increased Ii expression. The authors of these studies conclude that Nef functions may contribute directly to the impaired CD4(+)-T-helper-cell responses found in HIV-1-infected patients with progressive disease. The ability of Nef to interfere with MHC-II antigen presentation might play a role in AIDS pathogenesis. Importantly, interpreted through the perspective provided by the present invention, the ability of nef to increase CD74 expression has important implications for the activation of gamma delta T cells, NK cells, and NK T cells. In other words, nef may promote gamma delta T cell-mediated cell death of infected CD4 cells as a result of anomalous CD74/Ii/CLIP expression on the cell surface of CD4 T cells.

Toll-like receptor activation, resulting from pathogenic infection, can induce a powerful immune response. On susceptible genetic backgrounds, when TLRs recognize predominantly microbial products, the activation of these receptors by pathogens can induce the activation of cells that are implicated in autoimmunity. The involvement of microbial products, self antigens, and other TLR ligands in the onset of specific autoimmune diseases remains unclear. In the present invention, we suggest that the binding of TLR ligands on the appropriate genetic background will result in the ectopic expression of CLIP molecules, including but not limited to CLIP and intact CD74. It is the ectopic expression of these molecules that results in activation of $\gamma\delta T$ cells, NK cells, or NKT cells that mediate autoimmune sequelae. Reciprocally, the TLR ligands can be used to promote recognition and killing of tumor cells by the same effector cells ($\gamma\delta T$ cells, NK cells, and/or NKT cells).

Cell Types

A. B Cells

B lymphocytes are the precursors of antibody-producing cells. These cells express a cell surface form of antibody that is their receptor for antigen (also known as membrane immunoglobulin). Once antigen is bound by that receptor, the B cell is stimulated, the antigen that is bound by the receptor gets engulfed along with the receptor, where the complex is internalized in the B cell's endosomal system. Once inside the cell, the antigen-containing endosome fuses with a lysosome where antigen is broken down and loaded onto special molecules for transport to the cell surface. At the B cell surface, the newly processed antigen is associated with a molecular complex of MHC molecules that can be recognized by T lymphocytes. Recognition of antigen and MHC as a complex is a requirement for T cell activation and a normal immune response.

B cell maturation. B lymphocyte precursors, like all lymphoid precursors, are born in the bone marrow where they are derived from an even earlier precursor known as the hematopoietic "stem" cell. Once the precursor B cell has been given the "go ahead" to develop and mature, there is transcription and translation of the heavy chain for the "first-to-be-produced" antibody, immunoglobulin M or IgM, for short. In fact, the generation of messenger RNA for IgM designates the point at which that precursor cell is destined to be a B lymphocyte. The newly formed heavy chain eventually pairs with a precursor chain for a true light chain and then switches to become associated with one of two types of mature light chains, known as kappa or lambda, light chains. In both mice and humans, ninety-five percent of our light chains are kappa chains. Once the heavy chain covalently bonds by way of disulfide bonds to the light chains, the molecule gets transported to the B cell surface and the B cell is now said to be a pre-B cell—still resident in the bone marrow, but not fully mature. At this stage, the B cell is particularly vulnerable to deletion. When pre-B cells in the bone marrow encounter antigens (most likely "self" antigens) for which they are specific, the pre-B cell dies. This process of "clonal abortion" likely occurs to protect the pre-B cell from becoming self-reactive and from producing self-reactive antibodies. Presumably in the bone marrow, the majority of antigens are self. The suicidal death of the B cell prevents the maturation of self-reactive B cells and likely reflects that developmental pressure not to allow self-reactive B cells to enter the rest of the body.

The second isotype of heavy chain produced within the B cell while still in the bone marrow is the heavy chain for IgD molecules. This particular isotype, like the membrane version of IgM, gets transported to the cell surface once its transcription and translation have occurred and once it has been connected with light chains. Providing the B cell has not been removed by deletion, the developmental expression of cell surface IgM and cell surface IgD signal the newly matured B cell to exit the bone marrow and to go to the peripheral lymphoid tissues, including the circulation, the spleen, and the germinal centers of lymph nodes. Once the peripheral immune system has been populated with mature B cells, the B cells have a quite limited life span, unless they encounter the antigen for which they are specific. Once that happens and the B cell receives the necessary growth factors or other factors necessary for its development into an immunoglobulin secreting plasma cell, the B cell is protected from cell death. The large numbers of those that don't encounter antigen die by "neglect". Those that remain, for example, the daughter cells of the activated and expanding antigen-specific clones of B cells, are thought to be memory B cells. The memory cells are also thought to express the cell surface molecule CD27 and are thought to live for a long time, unlike the naïve, non-primed B cell. Recognizing antigen in the periphery is the first life-saving step for the B cell in this case.

Once the peripheral B cell encounters antigen, unless the antigen is a particular kind of bacterial (polymeric) antigen, the B cell will need additional "help" in the form of cytokines and even perhaps direct contact with CD4$^+$ T cells. The mechanism by which the CD4$^+$ T cell "helps" B cells to finish their peripheral maturation process is not completely understood. Most studies suggest that actual "cognate" interactions occur between the B cell and the T cell, while others suggest the T cell's production of cytokines is sufficient. Regardless, for the B cell to secrete all forms and isotypes of antibody with the exception of IgM and membrane IgD, the B cell needs T cell "help" to produce all forms of IgG, IgA, and IgE. The only T-independent antigens are those that are the highly polymeric type. When they are sufficient to signal B cell activation and differentiation into an antibody-secreting cell, the B cell will only make IgM. Reiterating, for production of all other isotypes of antibody, the B cell will need T cell help because most B cell responses to antigen are said to be T-dependent.

As the price of a given geographic quantity of land is often said to be dependent on "location, location, location," the same may be true for the isotype of antibody that the CD4+ T cell will eventually help the B cell to produce. For example, when B cells secrete antibody that will reside in secretions, the isotype of the antibody will be IgA. Ultimately the B cell that matures near areas of secretions, for example, near salivary glands, the genito-urinary areas, or in the lactating breast, will produce mature forms of IgA. These molecules exists as dimers of a typical antibody (2H, 2L chains) such that a mature IgA molecule will have two typical antibody units bounded by a small protein known as a secretory component and another small molecule called the J chain. Most scientists that study secretory IgA suggest that the two molecule structures protect the newly synthesized antibodies from the harsh and degradative environment of the secretory tracts. This type of antibody is very important to the newborn that acquires a front-line of defense from Mother's milk. The baby orally ingests Mom's secreted IgA and vicariously receives the protection from specific antigens that Mom's B cells have already encountered.

B cells as Antigen Presenting Cells. A unique feature of B cells involves the ability of the membrane immunoglobulin (that B cell antigen receptor) not only to recognize and bind to antigens very specifically and deliver an activation to the cell, but also to engulf the antigen into unique endosomal compartments which fuse with lysosomal compartments where the "receptor-engaged" antigen is broken down into fragments, loaded into MHC class II molecules, transported to the cell membrane and there antigens associated with MHC are available to be recognized by T lymphocytes. The ability of professional antigen presenting cells to present antigens to the T lymphocytes depends on processing the antigen in the endosomal/lysosomal compartment. The B lymphocyte is an extraordinary APC in that the engulfment of antigen by this particular APC, and unlike other phagocytes, is antigen specific.

B. "Professional" Antigen Presenting Cells

The professional antigen-presenting cells (APCs) are a subset of specialized cells express class II MHC, and include B cells, macrophages, microglia, dendritic cells, and Langerhans cells among others. Traditionally, the professional antigen-presenting cells of the myeloid lineage, dendritic cells and macrophages, have been viewed primarily as accessory cells, functioning simply to assist T cell activation. Recently, however, it has become clear that myeloid-lineage APCs exert a profound influence on T cells, regulating both the nature of the response (humoral versus cellular immunity) and, in some cases, even whether a response occurs at all (activation versus anergy).

C. T Cells

T lymphocytes, like B lymphocytes, arise from hematopoeitic stem cells in the bone marrow. However, unlike B cells, the pre-T cells travel to another peripheral lymphoid tissue, the thymus, where T lymphocyte maturation processes occur. Interestingly, the thymus, as a T cell development organ, reaches its maximum size and capacity in very early childhood around the age of 2 to 3 years and, at puberty, the thymus begins to involute—shrinking to a small rudiment of what it had been earlier. No one has unraveled exactly how the pre-T cell is recruited to homes to the thymus, but research has shown that once the cells arrive they may stay as long as two weeks before the mature, appropriate cells leave the thymus to circulate throughout the periphery.

The thymus is the place where the pre-T cell develops the ability to recognize an enormous repertoire of antigens presented by either MHC class I or MHC class II. The pre-T cells enter the thymus without receptors for antigen and MHC, without CD4, and without CD8. In the thymus, T cells acquire T cell receptors for antigen, and either CD4 or CD8. During the process, those T cells that will recognize antigen and MHC class I become CD8$^+$ T cells and those that recognize MHC class II and antigen become CD4$^+$ T cells. Both CD4 and CD8 positive cells have cell surface T cell receptors for antigen. If a T cell, either a CD4+ or a CD8+ T cell, recognizes "self" antigen and self MHC class I or self MHC class II in the thymus, that T cell is deleted. For most of the CD4$^+$ and CD8$^+$ T cells have T cell receptors that consist of an alpha chain and a beta chain. There are other, more recently described T cells that express receptors that are called gamma/delta T cell receptors. Interestingly, like the B cell receptor for antigen, each of the T cell receptor chains have variable and constant regions. T cells, like B cells, have antigen receptors that can bind millions of different antigens (but in the case of T cells only so long as the processed antigens are associated with MHC molecules). The diversity of T cell receptors is provided by the large number of possible variable regions the T cell receptor can have. Like the variable regions in B cell receptors, the development of the T cell receptor variable regions result from recombination of segments of DNA. However, unlike the B cell receptor for antigen, T cell receptor recombination occurs in the thymus, not in the bone marrow.

The developmental maturation of T cells in the thymus results in a high percentage of thymocyte cell death. Waves of cortisone kill many of the pre-T cells that don't meet the necessary requirements for recognition and survival. In addition to cortisone-dependent thymocyte cell death, recognition of antigen in the thymus deletes some potentially self-reactive T cells from the repertoire. The process of antigen-specific T cell death in the thymus is commonly referred to as "negative" selection. NOTE that CD4+ T cells in us would only get deleted if they recognize self MHC class I or MHC class II plus self antigen (like CLIP). (Those that could recognize CLIP and someone else's MHC class I or class II will not have been deleted—see below the discussion of invariant chain (Ii) and CLIP). Those CD4+ or CD8+ T cells that recognize SELF antigens associated with either class I or class II molecules will be deleted in the thymus. Those cells that meet all of the survival criterion, e.g. appropriate recognition of antigen and either MHC class I for the developing CD8$^+$ T or MHC class II for the developing CD4$^+$ T cell.

D. NK Cells

Natural killer cells (NK cells) are a population of lymphocytes which represent a very early line of defense against viruses and tumor cells. NK cells can be characterized by the presence of CD56 and CD16 markers and by the absence of the CD3 marker. NK cells are involved in non specific antitumoral immunity of antigens, to prevent the establishment of primitive or metastatic tumors in the immunocompetent or immunosuppressed host. NK cells appear to play a key role against tumor cells or negative class I MHC cell variants. Because of their non-specific cytotoxic properties for antigen and their efficacy, NK cells constitute a particularly important population of effector cells in the development of immunoadoptive approaches for the treatment of cancer or infectious diseases. NK cells have also been used for experimental treatment of different types of tumors.

Thus, in some aspects the invention relates to a method for treating a disorder associated with γδT cell expansion, activation and/or effector function by contacting a CLIP compound expressing cell with an inhibitor of γδT cell expansion, activation and/or effector function in an effective amount to interfere with γδT cell expansion, activation and/or effector function by the CLIP compound expressing cell. Alternatively the invention relates to treating such disorders in a subject by administering to the subject a CLIP inhibitor in an effective amount to reduce CLIP function in a CLIP compound expressing cell of the subject.

A disorder associated with γδT cell expansion, activation and/or effector function is one in which the expansion, activation or function of γδT cells places a pathogenic role in the disease. For instance the expansion and activation of the γδT cells by a cell expressing CLIP on the surface in the context of an MHC molecule causes such cells to accumulate in higher than normal amounts, such that they can act on other T cells or directly attack host tissue. An example of a disorder associated with γδT cell expansion, activation and/or effector function is autoimmune disease. It is believed that, according to an aspect of the invention, cells having CLIP on the surface in the context of MHC may cause the expansion and/or activation of these cells. Once the γδT cells are activated they may recognize CLIP in the context of MHC on host tissue such as neurons, pancreatic B cells and heart tissue. The result of that recognition may be the killing of the host cell. The γδT cells may also cause further production of antigen non-specific B cells which are capable of picking up host antigen and further producing a host specific immune response. Other disorders associated with γδT cell expansion, activation and/or effector function include HIV infection and rejection of transplanted cells, tissues or grafts. The activated γδT cell can mediate the killing of the transplanted cells and tissue as well as host T cells, that are critical in advancing the HIV infection.

A CLIP molecule expressing cell is a cell that has MHC class I or II on the surface and includes a CLIP molecule within that MHC. Such cells include B cell, a neuron, an oligodendrocyte, a microglial cell, or an astrocyte, a heart cell, a pancreatic beta cell, an intestinal epithelial cell, a lung cell, an epithelial cell lining the uterine wall, and a skin cell.

The CLIP molecule, as used herein, refers to intact CD74 (also referred to as invariant chain), as well as the naturally occurring proteolytic fragments thereof. CLIP is one of the naturally occurring proteolytic fragments thereof. The function of the CLIP molecule in this invention is mainly as an MHC class II chaperone. MHC class II molecules are heterodimeric complexes that present foreign antigenic peptides on the cell surface of antigen-presenting cells (APCs) to $CD4^+$ T cells. MHC class II synthesis and assembly begins in the endoplasmic reticulum (ER) with the non-covalent association of the MHC α and β chains with trimers of CD74. CD74 is a non-polymorphic type II integral membrane protein; murine CD74 has a short (30 amino acid) N-terminal cytoplasmic tail, followed by a single 24 amino acid transmembrane region and an ~150 amino acid long lumenal domain. Three MHC class II αβ dimers bind sequentially to a trimer of the CD74 to form a nonameric complex (αβIi)3, which then exits the ER. After being transported to the trans-Golgi, the αβIi complex is diverted from the secretory pathway to the endocytic system and ultimately to acidic endosome or lysosome-like structures called MHC class II compartments (MIIC or CIIV).

The N-terminal cytoplasmic tail of CD74 contains two extensively characterized dileucine-based endosomal targeting motifs. These motifs mediate internalization from the plasma membrane and from the trans-Golgi network. In the endocytic compartments, the CD74 chain is gradually proteolytically processed, leaving only a small fragment, the class II-associated CD74 chain peptide (CLIP), bound to the released αβ dimers. The final step for MHC class II expression requires interaction of αβ-LIP complexes with another class II-related αβ dimer, called HLA-DM in the human system. This drives out the residual CLIP, rendering the αβ dimers ultimately competent to bind antigenic peptides, which are mainly derived from internalized antigens and are also delivered to the endocytic pathway. The peptide-loaded class II molecules then leave this compartment by an unknown route to be expressed on the cell surface and surveyed by $CD4^+$ T cells.

The methods of this aspect of the invention my able accomplished using an inhibitor of γδT cell expansion, activation and/or effector function. Inhibitors of γδT cell expansion, activation and/or effector function are any molecules that reduce the presence of a CLIP molecule on the MHC, either directly or indirectly. An example of a γδT cell expansion, activation and/or effector function is a CLIP expression inhibitor. CLIP expression inhibitors are compounds that inhibit the expression of a CLIP molecule RNA. For instance CLIP expression inhibitors include antisense and siRNA. For instance, antisense or siRNA directed to a CLIP molecule or HLA-DO are useful as CLIP expression inhibitors. Antisense and siRNA as well as other expression inhibitors are described in more detail below.

Another type of γδT cell expansion, activation and/or effector function is a CLIP activity inhibitor. CLIP activity inhibitors include agents that displace CLIP, anti-CLIP molecule antibodies, recombinant HLA-DM and agents that inhibit CD74 processing. Many molecules are useful for displacing CLIP molecules. For instance compounds such as chloroquine, a lysosomatropic agent, or peptide/lipopeptide antigen are known to have such function. Other CLIP displacers include the small molecular compound pCP, chlorobenzene (CB), parachloroanisol (pCA), the peptides HA306-318 (PKYVKQNTLKLAT) (SEQ ID NO. 3), CO260-272 (IAGFKGEQGPKGE) (SEQ ID NO. 4), HLA binding peptides, and FRIMAVLAS (SEQ ID NO. 2).

Another agent that displaces CLIP is a halogenated alky ester. The halogenated alky ester is particularly useful in combination with a glycolytic inhibitor. The combination of agents may be administered separately or together. In some instances the combination of agents is in the form of a prodrug bifunctional molecule. Such materials are described in more detail below.

Anti-CLIP antibodies, which include antibodies that bind to CLIP molecules are also useful as agents that displace CLIP. Such antibodies are described in more detail below.

Other inhibitors of CLIP activity are agents that inhibit CD74 processing. Agents that inhibit CD74 processing are known in the art and include cystatin, A, B, or C.

In the methods of this aspect of the invention the CLIP expressing cell may also be exposed to an MHC class I or II loading peptide or an anti-MHC antibody. The purpose of exposing the cell to an MHC class I or II loading peptide or an anti-MHC class II antibody is to prevent the cell, once CLIP has been removed, from picking up a self antigen, which could be presented in the context of MHC. An MHC class I or II loading peptide is one that fits within the MHC groove, and in some embodiments will not provoke an interaction with other immune cells. For instance peptides such as FRIMAVLAS (SEQ ID NO. 2) function quite well as MHC class I or II loading peptides. One advantage of FRIMAVLAS (SEQ ID NO. 2) is that it functions as both a CLIP molecule displacer and an MHC class I or II loading peptide and thus only needs to be administered once.

An anti-MHC class II antibody may be administered in order to engage a B cell and kill it. Once CLIP has been removed, the antibody will be able to interact with the MHC and cause the B cell death. This prevents the B cell with an empty MHC from picking up and presenting self antigen or from getting another CLIP molecule in the surface that could lead to further γδT cell expansion and activation. MHC is Major Histocompatibility Complex. MHC encoded molecule class I (HLA-A, B, or C, HLA-E, F, or G, CD1a, b, c, or d), or Class II (HLA-DR, DP, or DQ; HLA-DM, HLA-DO) are generally useful in the invention.

The methods may also involve the removal of antigen non-specifically activated B cells and/or γδT cells from the subject to treat the disorder. The methods can be accomplished as described above alone or in combination with known methods for depleting such cells.

A subject shall mean a human or vertebrate mammal including but not limited to a dog, cat, horse, goat and primate, e.g., monkey. Thus, the invention can also be used to treat diseases or conditions in non human subjects. Preferably the subject is a human.

As used herein, the term treat, treated, or treating when used with respect to a disorder refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

A. AIDS or HIV-1 Infection

According to an embodiment of the invention, the methods described herein are useful in inhibiting the development of and/or treating AIDS or HIV-1 infections. In a specific embodiment, treatment is by inhibiting or reducing the expression or activity of CLIP molecules in, or blocking CLIP presentation by, CD4 T cells of a subject infected with HIV. In particular, CLIP molecules can be blocked by treatment with an agent that removes CLIP molecules from MHC, by treatment with an agent that prevents processing of CLIP molecules, or by contacting a CD4 T cell bearing CLIP with an anti-CLIP antibody or binding peptide.

Examples of agents that remove CD74 or CLIP are chloroquine, a lysosomatropic agent, or peptide/lipopeptide antigen. Examples of agents that reduce expression of CD74 and/or a proteolytic product thereof are antisense or siRNA to CLIP molecule/CD74 or CLIP or HLA-DO.

In another embodiment, treatment is by killing or inhibiting the function of antigen non-specifically activated B cells and/or γδT cells, in some cases vγ9vδ2 T cells, in a subject infected with HIV. Inhibiting function can include (a) removing antigen non-specifically activated B cells and/or γδT cells (or NK or NKT cells) from the subject, (b) removing TLR ligand-activated B cells, (c) removing other antigen presenting cells that results in cell surface expression of invariant chain/CD74 or CLIP so as to remove any of those that can express Ii/CD74 or CLIP on the cell surface, (d) selectively removing the cells that have any form of invariant chain on the surface, (e) inhibiting antigen non-specific activation of B cells in the subject, or (f) by antibody depletion of the B cells and/or the γδT cells. An anti-CLIP antibody can be obtained from BD Pharmingen or another commercial antibody source. Examples of antibodies are described below. An anti-γδT cell antibody also an be obtained from BD Pharmingen.

In accordance with another embodiment, the methods of this invention can be applied in conjunction with, or supplementary to, the customary treatments of AIDS or HIV-1 infection. Historically, the recognized treatment for HIV-1 infection is nucleoside analogs, inhibitors of HIV-1 reverse transcriptase (RT). Intervention with these antiretroviral agents has led to a decline in the number of reported AIDS cases and has been shown to decrease morbidity and mortality associated with advanced AIDS. Prolonged treatment with these reverse transcriptase inhibitors eventually leads to the emergence of viral strains resistant to their antiviral effects. Recently, inhibitors of HIV-1 protease have emerged as a new class of HIV-1 chemotherapy. HIV-1 protease is an essential enzyme for viral infectivity and replication. Protease inhibitors have exhibited greater potency against HIV-1 in vitro than nucleoside analogs targeting HIV-1 RT. Inhibition of HIV-1 protease disrupts the creation of mature, infectious virus particles from chronically infected cells. This enzyme has become a viable target for therapeutic intervention and a candidate for combination therapy.

Knowledge of the structure of the HIV-1 protease also has led to the development of novel inhibitors, such as saquinovir, ritonavir, indinivir and nelfinavir. NNRTIs (non-nucleoside reverse transcriptase inhibitors) have recently gained an increasingly important role in the therapy of HIV infection. Several NNRTIs have proceeded onto clinical development (i.e., tivirapine, loviride, MKC-422, HBY-097, DMP 266).

Nevirapine and delaviridine have already been authorized for clinical use. Every step in the life cycle of HIV-1 replication is a potential target for drug development.

Many of the antiretroviral drugs currently used in chemotherapy either are derived directly from natural products, or are synthetics based on a natural product model. The rationale behind the inclusion of deoxynucleoside as a natural based antiviral drugs originated in a series of publications dating back as early as 1950, wherein the discovery and isolation of thymine pentofuranoside from the air-dried sponges (*Cryptotethia crypta*) of the Bahamas was reported. A significant number of nucleosides were made with regular bases but modified sugars, or both acyclic and cyclic derivatives, including AZT and acyclovir. The natural spongy-derived product led to the first generation, and subsequent second-third generations of nucleosides (AZT, DDI, DDC, D4T, 3TC) antivirals specific inhibitors of HIV-1 RT.

A number of non-nucleoside agents (NNRTIs) have been discovered from natural products that inhibit RT allosterically. NNRTIs have considerable structural diversity but share certain common characteristics in their inhibitory profiles. Among NNRTIs isolated from natural products include: calanoid A from calophylum langirum; Triterpines from Maporonea African a. There are publications on natural HIV integrase inhibitors from the marine ascidian alkaloids, the lamellarin.

The role of HIV protease in the production of functionally infectious particle has been described as a critical process for retrovirus as well as HIV replication. The natural product, Pepstatin A, is a metabolite of streptomycin testaceus and *Streptomyces argentolus* var. *toyonakensis* was shown to inhibit HIV-1 Protease enzyme. The key strategy used in the development of the current HIV-1 protease inhibitors was to substitute the scissile P1-P1 amide bond by a nonhydrozable isoster with tetrahedral geometry; the designs were guided by assays and based on substrate specificity. It eventually led to the optimization of peptidomimetric lead structure and the development of novel class of protease inhibitors including indinvir, Saqunovir, nelfinavir and retinovir.

B. Transplant/Graft Rejection

The success of surgical transplantation of organs and tissue is largely dependent on the ability of the clinician to modulate the immune response of the transplant recipient. Specifically the immunological response directed against the transplanted foreign tissue must be controlled if the tissue is to survive and function. Currently, skin, kidney, liver, pancreas, lung and heart are the major organs or tissues with which allogeneic transplantations are performed. It has long been known that the normally functioning immune system of the transplant recipient recognizes the transplanted organ as "non-self" tissue and thereafter mounts an immune response to the presence of the transplanted organ. Left unchecked, the immune response will generate a plurality of cells and proteins that will ultimately result in the loss of biological functioning or the death of the transplanted organ.

This tissue/organ rejection can be categorized into three types: hyperacute, acute and chronic. Hyperacute rejection is essentially caused by circulating antibodies in the blood that are directed against the tissue of the transplanted organ (transplant). Hyperacute rejection can occur in a very short time—often in minutes—and leads to necrosis of the transplant. Acute graft rejection reaction is also immunologically mediated and somewhat delayed compared to hyperacute rejection. The chronic form of graft rejection that can occur years after the transplant is the result of a disease state commonly referred to as Graft Arterial Disease (GAD). GAD is largely a vascular disease characterized by neointimal proliferation of smooth muscle cells and mononuclear infiltrates in large and small vessels. This neointimal growth can lead to vessel fibrosis and occlusion, lessening blood flow to the graft tissue and resulting in organ failure. Current immunosuppressant therapies do not adequately prevent chronic rejection. Most of the gains in survival in the last decade are due to improvements in immunosuppressive drugs that prevent acute rejection. However, chronic rejection losses remain the same and drugs that can prevent it are a critical unmet medical need.

According to an embodiment of the invention, the methods described herein are useful in inhibiting cell graft or tissue graft rejection. Thus, the methods are useful for such grafted tissue as heart, lung, kidney, skin, cornea, liver, neuronal tissue or cell, or with stem cells, including hematopoetic or embryonic stem cells, for example. In accordance herewith, treatment can be by inhibiting or reducing the cell surface expression of CLIP molecules in cells of grafted tissue or cells, or by blocking CLIP molecule presentation by cells of a grafted tissue or cell.

Inhibiting or reducing cell surface expression of CLIP molecules includes treatment with an agent that removes or blocks CLIP molecules from MHC or that prevents processing of CD74 to CLIP. Examples of agents that remove CLIP molecules from MHC are chloroquine, a lysosomatropic agent, or peptide/lipopeptide antigen. Examples of agents that reduce expression of CLIP molecules are antisense or siRNA. To block CLIP molecule presentation, one can contact the grafted tissue with an anti-CLIP molecule antibody. Each of these methods is described above in more detail.

In accordance with another embodiment, the methods of this invention can be applied in conjunction with, or supplementary to, the customary treatments of transplant/graft rejection. Tissue graft and organ transplant recipients are customarily treated with one or more cytotoxic agents in an effort to suppress the transplant recipient's immune response against the transplanted organ or tissue. Current immunosuppressant drugs include: cyclosporin, tacrolimus (FK506), sirolimus (rapamycin), methotrexate, mycophenolic acid (mycophenolate mofetil), everolimus, azathiprine, steroids and NOX-100. All of these drugs have side effects (detailed below) that complicate their long-term use. For example, cyclosporin (cyclosporin A), a cyclic polypeptide consisting of 11 amino acid residues and produced by the fungus species *Tolypocladium inflatum* Gams, is currently the drug of choice for administration to the recipients of allogeneic kidney, liver, pancreas and heart (i.e., wherein donor and recipient are of the same species of mammals) transplants. However, administration of cyclosporin is not without drawbacks as the drug can cause kidney and liver toxicity as well as hypertension. Moreover, use of cyclosporin can lead to malignancies (such as lymphoma) as well as opportunistic infection due to the "global" nature of the immunosuppression it induces in patients receiving long term treatment with the drug, i.e., the hosts normal protective immune response to pathogenic microorganisms is downregulated thereby increasing the risk of infections caused by these agents. FK506 (tacrolimus) has also been employed as an immunosuppressive agent as a stand-alone treatment or in combination. Although its immunosuppressive activity is 10-100 times greater than cyclosporin, it still has toxicity issues. Known side effects include kidney damage, seizures, tremors, high blood pressure, diabetes, high blood potassium, headache, insomnia, confusion, seizures, neuropathy, and gout. It has also been associated with miscarriages. Methotrexate is commonly added to the treatment of the cytotoxic agent. Methotrexate is given in small doses several times after the transplant. Although the combination of cyclosporin and methotrexate has been found to be effective in decreasing the severity of transplant rejection, there are side effects, such as mouth sores and liver damage. Severe transplant rejection can be treated with steroids. However, the side effects of steroids can be extreme, such as weight gain, fluid retention, elevated blood sugar, mood swings, and/or confused thinking.

Rapamycin, a lipophilic macrolide used as an anti-rejection medication can be taken in conjunction with other anti-rejection medicines (i.e., cyclosporin) to reduce the amount of toxicity of the primary cytotoxic agent, but it too has specific side effects, such as causing high cholesterol, high triglycerides, high blood pressure, rash and acne. Moreover, it has been associated with anemia, joint pain, diarrhea, low potassium and a decrease in blood platelets.

When used in combination with the therapies of the invention the dosages of known therapies may be reduced in some instances, to avoid side effects.

C. Autoimmune disease

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

According to an embodiment of the invention, the methods described herein are useful in inhibiting the development of an autoimmune disease comprising inhibiting, in a subject, the cell surface expression of CLIP molecules by an antigen presenting cell or blocking CLIP molecule presentation to a γδT cell such as a vγ9vδ2 T cell. Thus, the methods are useful for such autoimmune diseases as multiple sclerosis, systemic lupus erythematosus, type 1 diabetes, viral endocarditis, viral encephalitis, rheumatoid arthritis, Graves' disease, autoimmune thyroiditis, autoimmune myositis, and discoid lupus erythematosus.

In accordance herewith, treatment can be by inhibiting or reducing the cell surface expression of CLIP molecules in cells, or by blocking CLIP molecules presentation. Inhibiting or reducing cell surface expression of CLIP molecules includes treatment with an agent that removes or blocks CLIP molecules from MHC or that prevents processing of CD74 to CLIP. Examples of agents that remove CLIP molecules from MHC are chloroquine, a lysosomatropic agent, or peptide/lipopeptide antigen. Examples of agents that reduce expression of CLIP molecules are antisense or siRNA. To block CLIP presentation, one can contact the grafted tissue with an anti-CLIP molecule antibody. Each of these methods is described above in more detail.

D. Diagnosing Autoimmune Disease, HIV and Tissue Graft Rejection

According to an embodiment of the invention, the methods described herein are useful in diagnosing autoimmune disease, HIV infection and tissue graft rejection such as multiple sclerosis, systemic lupus erythematosus, type 1 diabetes, viral endocarditis, viral encephalitis, rheumatoid arthritis, Graves' disease, autoimmune thyroiditis, autoimmune myositis, and discoid lupus erythematosus. The method involves measuring levels of at least one defensin in a subject exhibiting one or more additional symptoms of these diseases. In a specific embodiment, the defensin is LL37.

Defensins are family of potent antibiotics made within the body by neutrophils and macrophages, and play important roles against invading microbes. They act against bacteria, fingi and viruses by binding to their membranes and increasing membrane permeability. On a chemical level, the defensins are small peptides unusually rich in the amino acid cysteine (Cys). The human defensins are classified into the α-defensins and β-defensins on the basis of their sequence homology and their Cys residues. In accordance with this invention, defensins can serve as a marker for these diseases. For example γδT cell mediated autoimmunity may be diagnosed by determining the blood levels of defensins that are produced by γδT cells that are destructive. Levels of defensin at or above detectable levels means there are activated γδT cells and they are likely a pathogenic component of any form of autoimmune disease.

E. Cancer

According to an embodiment of the invention, the methods described herein are useful in treating cancers, tumors, and other conditions involving rapidly dividing cell populations that are typically uncontrolled. A "rapidly dividing cell," as used herein, is a cell which is undergoing mitotic growth. Such cells are well known in the art and include, but are not limited to, tumor cells, cancer cells, lymphocytes (T cells or B cells), bacteria, and pancreatic beta (β) cells. In these aspects of the invention it is desirable to activate γδT cells that can kill the rapidly dividing cells. The methods may be accomplished using a CLIP inducing agent.

A CLIP inducing agent as used herein refers to a compound that results in increased CLIP molecule presentation on the cell surface in the context of MHC. CLIP inducing agents include, for instance, CLIP expression vectors and CLIP activators. A CLIP expression vector is a vector that when administered to the cells causes production of a CLIP molecule protein. The CLIP molecule protein may be CD74, for instance. In the case that CD74 is produced it is desired that the CD74 be produced in the cell such that it can be processed intracellularly to produce a CLIP associated with MHC. Alternatively it may be processed in other cells that are capable of secreting it such that CD74 protein is capable of interacting with MHC on the surface. The expression vector may also produce a CLIP peptide either intracellularly or extracellularly.

CLIP activators include for instance soluble nef or an agent that increases nef expression such as a nef expression vector. CLIP activators also include ectopic CLIP, palmitoylated protein or PAM, and an anti-CD40 or CD40L molecule in combination with IL-4. An HLA-DO molecule which promotes a higher HLA-DO:HLA-DM ratio is also a CLIP activator. A high HLA-DO:HLA-DM ratio causes the cell to produce more CLIP on the cell surface. Another molecule that is capable of achieving a high HLA-DO:HLA-DM ratio is an anti-sense or siRNA to HLA-DM. These compounds are described in more detail herein.

In a specific embodiment of the invention, cancer cells in a subject are killed by (1) treating the patient directly with soluble CLIP protein (can be made by proteolytic cleavage of recombinant invariant chain, simply making recombinant CLIP, or synthetic CLIP to activate a Th 1 response; (2) (a) inducing cell surface expression of CLIP on a B cell, preferably ex vivo; (b) contacting the B cell of step (a) with a γδT cell or NK cell, preferably in vivo, and (c) contacting the γδT cell or NK cell with the cancer cell. In particular embodiments, the γδT cell is a vγ9vδ2 T cell. In still other particular embodiments, the B cell of step (a) and/or the γδT cell of step (c) and/or the NK cell is allogeneic to the subject.

In accordance with an embodiment of the invention, the cancer cells are killed by inducing cell surface expression of CLIP in the cancer cell. One method of inducing cell surface expression of CLIP in the cancer cell is to treat the cancer cells with nef or an agent that increases nef expression. Thus one can use gene targeting to express the nef gene in the cancer cell by exposing the cancer cell to the soluble products of recombinant nef expressed in a mammalian vector. Another method is to treat the cancer cells with the protein product of the nef gene, the nef protein, Another method is to treat the tumor directly with CLIP, and gene target nef to the tumor so that only the tumor expresses invariant chain/CD74, or proteolytic products such as CLIP.

Another method is to treat the cancer cells with agent that will induce ectopic CLIP. For this procedure one can determine if the cancer in question expresses Toll-like receptors (TLRs) and can then treat the cancer patient with ligands for the TLR expressed on the cancer cell. The invention predicts that TLR engagement will result in the ectopic expression of CLIP on the surface of the cancer cell. Examples of inflammatory mediators that can be used to treat tumors include palmitoylated proteins, such as PAM—a synthetic TLR2 ligand, Pam(3)Cys-Ser-(Lys)(4) (Pam(3)CSK(4) and other palmitoylated proteins from bacterial products. These ligands will promote an increase in cell surface invariant chain/CD74 CLIP and thereby make the tumor cell a target for γδT cell killing.

Still another method is to treating the cancer cells with an inflammatory mediator such as palmitoylated proteins, such as PAM—a synthetic TLR2 ligand, Pam(3)Cys-Ser-(Lys)(4) (Pam(3)CSK(4), or other palmitoylated proteins from bacterial products.

In further embodiments, the method further comprising treating the subject with a standard anti-cancer therapy, for example chemotherapy, radiotherapy or hormonal therapy.

In any of the foregoing treatments, the agent can be introduced into the patient by any conventional means.

In particular embodiments, the cancer cell is a breast cancer cell, a lung cancer cell, a head & neck cancer cell, a brain cancer cell, an esophageal cancer cell, a liver cancer cell, a prostate cancer cell, a stomach cancer cell, an ovarian cancer cell, a uterine cancer cell, a cervical cancer cell, a testicular cancer cell, a skin cancer cell, a colon cancer cell, a leukemia cell, or a lymphoma cell. In other embodiments, the cancer cell is a glioblastoma cell, a rhabdomyosarcoma cell, a melanoma cell, or a Kaposi's sarcoma cell. In still other embodiments, the cancer is primary, metastatic, recurrent or multi-drug resistant.

Thus, the methods of the invention, in some embodiments, are useful for inducing cell death in many types of mammalian cells, and particularly in tumor cells. The term "cell death" is herein to refer to either of the processes of apoptosis or cell lysis. In both apoptosis and cell lysis, the cell dies, but the processes occur through different mechanisms and/or different metabolic states of the cell. Apoptosis is a process of cell death in which the cell undergoes shrinkage and fragmentation, followed by phagocytosis of the cell fragments. Apoptosis is well known in the art and can be assessed by any art-recognized method. For example, apoptosis can easily be determined using flow cytometry, which is able to distinguish between live and dead cells.

In one set of embodiments, the invention includes a method of treating a subject susceptible to or exhibiting symptoms of cancer. In some cases, the cancer is drug-resistant or multi-drug resistant. As used herein, a "drug-resistant cancer" is a cancer that is resistant to conventional commonly-known cancer therapies. Examples of conventional cancer therapies include treatment of the cancer with agents such as methotrexate, trimetrexate, adriamycin, taxotere, doxorubicin, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, etc. A "multi-drug resistant cancer" is a cancer that resists more than one type or class of cancer agents, i.e., the cancer is able to resist a first drug having a first mechanism of action, and a second drug having a second mechanism of action.

In one embodiment, the methods of the invention can be used in conjunction with one or more other forms of cancer treatment, for example, in conjunction with an anti-cancer agent, chemotherapy, radiotherapy, etc. (e.g., simultaneously, or as part of an overall treatment procedure). As another non-limiting example, a cell may be manipulated to increase the amount of UCP or Fas in the plasma membrane, and also exposed to another form of cancer treatment. The term "cancer treatment" as used herein, may include, but is not limited to, chemotherapy, radiotherapy, adjuvant therapy, vaccination, or any combination of these methods. Parameters of cancer treatment that may vary include, but are not limited to, dosages, timing of administration or duration or therapy; and the cancer treatment can vary in dosage, timing, or duration. Another treatment for cancer is surgery, which can be utilized either alone or in combination with any of the previously treatment methods. One of ordinary skill in the medical arts can determine an appropriate treatment for a subject.

A "tumor cell," as used herein, is a cell which is undergoing unwanted mitotic proliferation. A tumor cell, when used in the in vitro embodiments of the invention, can be isolated from a tumor within a subject, or may be part of an established cell line. A tumor cell in a subject may be part of any type of cancer. Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer. In general, an effective amount of a composition for treating a cancer will be that amount necessary to inhibit mammalian cancer cell proliferation in situ. Those of ordinary skill in the art are well-schooled in the art of evaluating effective amounts of anti-cancer agents.

In some cases, the cancer treatment may include treatment with an anti-cancer agent or drug, for example, a conventionally-known anti-cancer agent or drug. Examples of suitable anti-cancer agents and drugs include, but are not limited to, methotrexate, trimetrexate, adriamycin, taxotere, 5-fluorouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, and goserelin acetate. Additional examples of suitable anti-cancer agents and drugs include, but are not limited to, 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, caracemide, carbetimer, carboplatin, carboxamide-amino-triazole, carboxyamidotriazole, carest M3, carmustine, carn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, dichloroacetate, didemnin B, didox, diethylnorspermine, dihydro-5-azacytidine, dioxamycin, diphenyl spiromustine, docosanol, dolasetron, doxifluridine, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, and zorubicin hydrochloride, as well as salts, homologs, analogs, derivatives, enantiomers and/or functionally equivalent compositions thereof.

In another embodiment, cells may be removed from a tumor or other rapidly dividing cell mass (e.g., a tumor from a subject, a tumor growing in vitro, etc.) and exposed in some fashion to the methods described herein, including treatment with TLR ligands or inflammatory agents to increase cell surface expression of invariant chain/CD74, and/or CLIP. After suitable exposure, the exposed cells may be introduced into a subject. Exposure of the cells may alter the immunological profile of the tumor cells in some fashion, for example, such that a subject's immune system is able to recognize the tumor cells. The subject's immune system, after interacting with the exposed cells, may then be able to recognize tumors present within the subject, thus causing the cancer (or other rapidly dividing cell mass) to decrease. If the subject has a tumor, the cells may be injected into the tumor, proximate the tumor, and/or systemically or locally delivered in a region of the body away from the tumor. In some cases, a tumor may be removed from a subject, then the exposed cells may be inserted, e.g., into the cavity created upon removal of the tumor, or to another site within the body. Optionally, other cancer treatment methods, such as radiation or exposure to conventional anti-cancer agents, may also be used in conjunction with these methods. In some cases, the subject may not have a cancer or tumor, but the cells may be injected to stimulate the immune system to produce antibodies against future cancers and/or other uncontrolled cellular growths, i.e., "immunizing" the subject from cancer and/or other uncontrolled cellular growths. In some the cancer cells are antigenic and can be targeted by the immune system. Thus, the combined administration of the methods of the invention and cancer medicaments, particularly those which are classified as cancer immunotherapies, can be very useful for stimulating a specific immune response against a cancer antigen.

A "cancer antigen" as used herein is a compound, such as a peptide, associated with a tumor or cancer cell surface, and which is capable of provoking an immune response when expressed on the surface of an antigen-presenting cell in the context of an MHC molecule. Cancer antigens, such as those present in cancer vaccines or those used to prepare cancer immunotherapies, can be prepared from crude cancer cell extracts, e.g., as described in Cohen et al. (1994), or by partially purifying the antigens, using recombinant technology, or de novo synthesis of known antigens. Cancer antigens can be used in the form of immunogenic portions of a particular antigen, or in some instances, a whole cell or a tumor mass can be used as the antigen. Such antigens can be isolated or prepared recombinantly or by any other means known in the art.

The methods of the invention can be used in combination with immunotherapeutics, according to another embodiment. The goal of immunotherapy is to augment a subject's immune response to an established tumor. One method of immunotherapy includes the use of adjuvants. Adjuvant substances derived from microorganisms, such as *Bacillus Calmette-Guerin*, can heighten the immune response and enhance resistance to tumors in animals. Immunotherapeutic agents are often medicaments which derive from antibodies or antibody fragments that specifically bind to or otherwise recognize a cancer antigen. Binding of such agents can promote an immune response, such as an antigen-specific immune response. Antibody-based immunotherapy may function by binding to the cell surface of a cancer cell, which can stimulate the endogenous immune system to attack the cancer cell.

As used herein, a "cancer antigen" is broadly defined as an antigen expressed by a cancer cell. The antigen can be expressed at the cell surface of the cancer cell. In many cases, the antigen is one which is not expressed by normal cells, or at least not expressed at the same level or concentration as in cancer cells. As examples, some cancer antigens are normally silent (i.e., not expressed) in normal cells, some are expressed only at certain stages of differentiation, and others are only temporally expressed (such as embryonic and fetal antigens). Other cancer antigens are encoded by mutant cellular genes, such as oncogenes (e.g., activated ras oncogene), suppressor genes (e.g., mutant p53), fusion proteins resulting from internal deletions or chromosomal translocations, or the like. Still other cancer antigens can be encoded by viral genes, such as those carried on RNA and DNA tumor viruses. The differential expression of cancer antigens in normal and cancer cells can be exploited in order to target cancer cells in some cases. As used herein, the terms "cancer antigen" and "tumor antigen" are used interchangeably.

The theory of immune surveillance is that a prime function of the immune system is to detect and eliminate neoplastic cells before a tumor forms. A basic principle of this theory is that cancer cells are antigenically different from normal cells and thus can elicit immune reactions similar to those that cause rejection of immunologically incompatible allografts. Studies have confirmed that tumor cells differ, qualitatively or quantitatively, in their expression of antigens. For example, "tumor-specific antigens" are antigens that are specifically associated with tumor cells but not normal cells. Examples of tumor specific antigens are viral antigens in tumors induced by DNA or RNA viruses. "Tumor-associated" antigens are present in both tumor cells and normal cells but are present in a different quantity or a different form in tumor cells. Examples of such antigens are oncofetal antigens (e.g., carcinoembryonic antigen), differentiation antigens (e.g., T and Tn antigens), and oncogene products (e.g., HER/neu).

Different types of cells that can kill tumor targets in vitro and in vivo have been identified: natural killer cells (NK cells), cytolytic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses. LAK cells are a subset of null lymphocytes distinct from the NK and CTL populations. Activated macrophages can kill tumor cells in a manner that is not antigen-dependent, nor MHC-restricted, once activated. Activated macrophages are thought to decrease the growth rate of the tumors they infiltrate. In vitro assays have identified other immune mechanisms such as antibody-dependent, cell-mediated cytotoxic reactions, and lysis by antibody plus complement. However, these immune effector mechanisms are thought to be less important in vivo than the function of NK, CTLs, LAK, and macrophages in vivo (for a review, see Piessens (1996).

In some cases, the immunotherapeutic agent may function as a delivery system for the specific targeting of toxic substances to cancer cells. For example, the agent may be conjugated to toxins such as ricin (e.g., from castor beans), calicheamicin, maytansinoids, radioactive isotopes such as iodine-131 and yttrium-90, chemotherapeutic agents, and/or to biological response modifiers. In this way, the toxic substances can be concentrated in the region of the cancer and non-specific toxicity to normal cells can be minimized.

In certain instances, the immunotherapeutic agent may be directed towards the binding of vasculature, such as those which bind to endothelial cells. This is because solid tumors are generally dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

In another set of embodiments, the combined administration of the methods of the invention and an apoptotic chemotherapeutic agent may be used. An "apoptotic chemotherapeutic agent," as used herein, includes molecules which function by a variety of mechanisms to induce apoptosis in rapidly dividing cells. Apoptotic chemotherapeutic agents are a class of chemotherapeutic agents which are well known to those of ordinary skill in the art. Chemotherapeutic agents include those agents disclosed in Goodman and Gilman's Chapter 52, and the introduction thereto, (1990), incorporated herein by reference. Suitable chemotherapeutic agents may have various mechanisms of action. Classes of suitable chemotherapeutic agents include, but are not limited to: (a) alkylating agents, such as nitrogen mustard (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, which is also known as BCNU, lomustine which is also known as CCNU, semustine, which is also known as methyl-CCNU, chlorozoticin, streptozocin), and triazines (e.g., dicarbazine, which is also known as DTIC); (b) antimetabolites, such as folic acid analogs (e.g., methotrexate), pyrimidine analogs (e.g., 5-fluorouracil floxuridine, cytarabine, and azauridine and its prodrug form azaribine), and purine analogs and related materials (e.g., 6-mercaptopurine, 6-thioguanine, pentostatin); (c) natural products, such as the vinca alkaloids (e.g., vinblastine, vincristine), epipodophylotoxins (e.g., etoposide, teniposide), antibiotics (e.g., dactinomycin, which is also known as actinomycin-D, daunorubicin, doxorubicin, bleomycin, plicamycin, mitomycin, epirubicin, which is 4-epidoxorubicin, idarubicin which is 4-dimethoxydaunorubicin, and mitoxanthrone), enzymes (e.g., L-asparaginase), and biological response modifiers (e.g., interferon α); (d) miscellaneous agents, such as the platinum coordination complexes (e.g., cisplatin, carboplatin), dichloroacetate and its derivatives, substituted ureas (e.g., hydroxyurea), methylhydiazine derivatives (e.g., procarbazine), adreocortical suppressants (e.g., mitotane, aminoglutethimide) taxol; (e) hormones and antagonists, such as adrenocorticosteroids (e.g., prednisone or the like), progestins (e.g., hydroxyprogesterone caproate, medroxyprogesterone acetate, megestrol acetate), estrogens (e.g., diethyestilbestrol, ethinyl estradiol, or the like), antiestrogens (e.g., tamoxifen), androgens (e.g., testosterone propionate, fluoxymesterone, or the like), antiandrogens (e.g., flutamide), and gonadotropin-releasing hormone analogs (e.g., leuprolide), and (f) DNA damaging compounds, such as adriamycin. The combined administration of the methods of the invention and an apoptotic chemotherapeutic agent effective to inhibit growth of the tumor cell is that amount effective to induce apoptosis of the tumor cell in some cases.

In yet another set of embodiments, the methods of the invention may be used in conjunction with a vaccine, such as a cancer vaccine. Cancer vaccines are medicaments which are intended to stimulate an endogenous immune response against cancer cells. Currently-produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells.

Although cancer vaccines may take one of several forms, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. Lysates of tumor cells can also be used as cancer vaccines to elicit an immune response in certain cases. Another form of cancer vaccine is a peptide vaccine which uses cancer-specific or cancer-associated small proteins to activate T cells. Cancer-associated proteins are proteins which are not exclusively expressed by cancer cells (i.e., other normal cells may still express these antigens). However, the expression of cancer-associated antigens is generally consistently upregulated with cancers of a particular type. Yet another form of cancer vaccine is a dendritic cell vaccine which includes whole dendritic cells that have been exposed to a cancer antigen or a cancer-associated antigen in vitro. Lysates or membrane fractions of dendritic cells may also be used as cancer vaccines in some instances. Dendritic cell vaccines are able to activate antigen-presenting cells directly. Other non-limiting examples of cancer vaccines include ganglioside vaccines, heat-shock protein vaccines, viral and bacterial vaccines, and nucleic acid vaccines.

Other cancer vaccines can take the form of dendritic cells which have been exposed to cancer antigens in vitro, have processed the antigens and are able to express the cancer antigens at their cell surface in the context of MHC molecules for effective antigen presentation to other immune system cells.

In some embodiments, cancer vaccines may be used along with adjuvants. Adjuvants are substances which activate the subject's immune system, and can be used as an adjunct therapy in any of the systems or methods of the invention. Adjuvants include, for example, alum, QS-Stimulon (Aquila), MF-59 (Chiron), Detox (Ribi), Optivax (Vaxcels) and LeIF (Corixa).

F. Infection

According to an embodiment of the invention, the methods described herein are useful in treating a intracellular bacterial infection in a subject by inducing cell surface expression of CLIP in an antigen presenting cell or by treating directly with soluble, synthetic CLIP or activating γδT cells. Specific methods of inducing cell surface expression of CLIP in the cell have been described above under the description related to methods of treating cancer. Examples are treating the cell with nef or an agent that increases nef expression, with ectopic CLIP, or with an inflammatory mediator such as Pam (3)Cys-Ser-(Lys)(4) (Pam(3)CSK(4).

The present invention would have applications therefore in the prevention and treatment of diseases against which a T cell response would be effective. The following pathogenic virus classes, which are mentioned by way of example, are specifically contemplated as targets for T cell selecting peptide administration: influenza A, B and C, parainfluenza, paramyxoviruses, Newcastle disease virus, respiratory syncytial virus, measles, mumps, parvoviruses, Epstein-Barr virus, rhinoviruses, coxsackieviruses, echoviruses, reoviruses, rhabdoviruses, lymphocytic choriomeningitis, coronavirus, polioviruses, herpes simplex, human immunodeficiency viruses, cytomegaloviruses, papillomaviruses, virus B, varicella-zoster, poxviruses, rubella, rabies, picornaviruses, rotavirus and Kaposi associated herpes virus.

In addition to the viral diseases mentioned above, the present invention is also useful in the prevention, inhibition, or treatment of bacterial infections, including, but not limited to, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other viridans streptococci, peptostreptococci, other related species of streptococci, enterococci such as *Enterococcus faecalis, Enterococcus faecium*, staphylococci, such as *Staphylococcus epidermidis, Staphylococcus aureus, Hemophilus influenzae*, pseudomonas species such as *Pseudomonas aeruginosa, Pseudomonas pseudomallei, Pseudomonas mallei*, brucellas such as *Brucella melitensis, Brucella suis, Brucella abortus, Bordetella pertussis, Borellia* species, such as *Borellia burgedorferi Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides, Bacteroides* species, *Actinomycetes* species, *Treponema pallidum, Leptospirosa* species, *Haemophilus* species, *Helicobacter* species, including *Helicobacter pylori, Treponema* species and related organisms. The invention may also be useful against gram negative bacteria such as *Klebsiella pneumoniae, Escherichia coli, Proteus, Serratia* species, *Acinetobacter, Yersinia pestis, Francisella tularensis, Enterobacter* species, *Bacteriodes* and *Legionella* species, *Shigella species, Mycobacterium* species (e.g., *Mycobacterium tuberculosis, Mycobacterium bovis* or other mycobacteria infections), *Mycobacterium avium* complex (MAC), *Mycobacterium marinum, Mycobacterium fortuitum, Mycobacterium kansaii, Yersinia* infections (e.g., *Yersinia pestis, Yersinia enterocolitica* or *Yersinia pseudotuberculosis*) and the like. In addition, the invention in contemplated to be of use in controlling protozoan, helminth or other macroscopic infections by organisms such as *Cryptosporidium, Entamoeba, Plamodiium, Giardia, Leishmania, Trypanasoma, Trichomonas, Naegleria, Isospora belli, Toxoplasma gondii, Trichomonas vaginalis, Wunchereria, Ascaris, Schistosoma* species, *Cyclospora* species, for example, and for *Chlamydia trachomatis* and other *Chlamydia* infections such as *Chlamydia psittaci*, or *Chlamydia pneumoniae*, for example. Of course it is understood that the invention may be used on any pathogen against which an effective antibody can be made.

Fungal and other mycotic pathogens (some of which are described in Human Mycoses (1979; Opportunistic Mycoses of Man and Other Animals (1989); and Scrip's Antifungal Report (1992), are also contemplated as a target of administration of a T cell selecting peptide. Fungi disease contemplated in the context of the invention include, but are not limited to, Aspergillosis, Black piedra, Candidiasis, Chromomycosis, Cryptococcosis, Onychomycosis, or *Otitis externa* (otomycosis), Phaeohyphomycosis, Phycomycosis, *Pityriasis versicolor*, ringworm, *Tinea barbae, Tinea capitis, Tinea corporis, Tinea cruris, Tinea favosa, Tinea imbricata, Tinea manuum, Tinea nigra* (palmaris), *Tinea pedis, Tinea unguium*, Torulopsosis, *Trichomycosis axillaris*, White piedra, and their synonyms, to severe systemic or opportunistic infections, such as, but not limited to, Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and Torulopsosis, and their synonyms, some of which may be fatal. Known fungal and mycotic pathogens include, but are not limited to, *Absidia* spp., *Actinomadura madurae, Actinomyces* spp., *Allescheria boydii, Alternaria* spp., *Anthopsis deltoidea, Apophysomyces elegans, Arnium leoporinum, Aspergillus* spp., *Aureobasidium pullulans, Basidiobolus ranarum, Bipolaris* spp., *Blastomyces dermatitidis, Candida* spp., *Cephalosporium* spp., *Chaetoconidium* spp., *Chaetomium* spp., *Cladosporium* spp., *Coccidioides immitis, Conidiobolus* spp., *Corynebacterium tenuis, Cryptococcus* spp., *Cunninghamella bertholletiae, Curvularia* spp., *Dactylaria* spp., *Epidermophyton* spp., *Epidermophyton floccosum, Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur, Microsporum* spp., *Mucor* spp., *Mycocentrospora acerina, Nocardia* spp., *Paracoccidioides brasiliensis, Penicillium* spp., *Phaeosclera dematioides, Phaeoannellomyces* spp., *Phialemonium obovatum, Phialophora* spp., *Phoma* spp., *Piedraia hortai, Pneumocystis carinii, Pythium insidiosum, Rhinocladiella aquaspersa, Rhizomucor pusillus, Rhizopus* spp., *Saksenaea vasiformis, Sarcinomyces phaeomuriformis, Sporothrix schenckii, Syncephalastrum racemosum, Taeniolella boppii, Torulopsosis* spp., *Trichophyton* spp., *Trichosporon* spp., *Ulocladium chartarum, Wangiella dermatitidis, Xylohypha* spp., *Zygomyetes* spp. and their synonyms. Other fungi that have pathogenic potential include, but are not limited to, *Thermomucor indicae-seudaticae, Radiomyces* spp., and other species of known pathogenic genera.

In some aspects, the invention provides methods and kits that include anti-CLIP molecule and anti-HLA binding molecules such as peptides, antibodies, antibody fragments and small molecules. CLIP and HLA binding molecules bind to CLIP molecules and HLA respectively on the surface of cells. The binding molecules are referred to herein as isolated molecules that selectively bind to CLIP molecules and HLA. A molecule that selectively binds to CLIP and HLA as used herein refers to a molecule, e.g, small molecule, peptide, antibody, fragment, that interacts with CLIP and HLA. In some embodiments the molecules are peptides.

The peptides minimally comprise regions that bind to CLIP and HLA. CLIP and HLA-binding regions, in some embodiments derive from the CLIP and HLA-binding regions of known or commercially available antibodies, or alternatively, they are functionally equivalent variants of such regions. The term "antibody" herein is used in the broadest sense and specifically covers intact monoclonal antibodies, polyclonal antibodies, multispecific antibodies (e.g. bispecific antibodies) formed from at least two intact antibodies, antibody fragments, so long as they exhibit the desired biological activity, and antibody like molecules such as scFv. A native antibody usually refers to heterotetrameric glycoproteins composed of two identical light (L) chains and two identical heavy (H) chains. Each heavy and light chain has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

Numerous CLIP and HLA antibodies are available commercially for research purposes. Certain portions of the variable domains differ extensively in sequence among antibodies and are used in the binding and specificity of each particular antibody for its particular antigen. However, the variability is not evenly distributed throughout the variable domains of antibodies. It is concentrated in three or four segments called "complementarity-determining regions" (CDRs) or "hypervariable regions" in both in the light-chain and the heavy-chain variable domains. The more highly conserved portions of variable domains are called the framework (FR). The variable domains of native heavy and light chains each comprise four or five FR regions, largely adopting a β-sheet configuration, connected by the CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., NIH Publ. No. 91-3242, Vol. I, pages 647-669 (1991)). The constant domains are not necessarily involved directly in binding an antibody to an antigen, but exhibit various effector functions, such as participation of the antibody in antibody-dependent cellular toxicity.

A hypervariable region or CDR as used herein defines a subregion within the variable region of extreme sequence variability of the antibody, which form the antigen-binding site and are the main determinants of antigen specificity. According to one definition, they can be residues (Kabat nomenclature) 24-34 (L1), 50-56 (L2) and 89-97 (L3) in the light chain variable region and residues (Kabat nomenclature 31-35 (H1), 50-65 (H2), 95-102 (H3) in the heavy chain variable region. Kabat et al., Sequences of Proteins of Immunological Interest, 5th Ed. Public Health Service, National Institute of Health, Bethesda, Md. [1991]).

An "intact" antibody is one which comprises an antigen-binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variant thereof. Preferably, the intact antibody has one or more effector functions. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture.

"Antibody fragments" comprise a portion of an intact antibody, preferably the antigen binding or variable region of the intact antibody. Examples of antibody fragments include Fab, Fab', F(ab')$_2$, and Fv fragments; diabodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CHl) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The "hinge region," and variations thereof, as used herein, includes the meaning known in the art, which is illustrated in, for example, Janeway et al., Immuno Biology: the immune system in health and disease, (Elsevier Science Ltd., NY) (4th ed., 1999)

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa (K) and lambda (O), based on the amino acid sequences of their constant domains.

The peptides useful herein are isolated peptides. As used herein, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

The CLIP and HLA binding molecules bind to CLIP and HLA, preferably in a selective manner. As used herein, the terms "selective binding" and "specific binding" are used interchangeably to refer to the ability of the peptide to bind with greater affinity to CLIP and HLA and fragments thereof than to non-CLIP and HLA derived compounds. That is, peptides that bind selectively to CLIP and HLA will not bind to non-CLIP and HLA derived compounds to the same extent and with the same affinity as they bind to CLIP and HLA and fragments thereof, with the exception of cross reactive antigens or molecules made to be mimics of CLIP and HLA such as peptide mimetics of carbohydrates or variable regions of anti-idiotype antibodies that bind to the CLIP and HLA-binding peptides in the same manner as CLIP and HLA. In some embodiments, the CLIP and HLA binding molecules bind solely to CLIP and HLA and fragments thereof.

"Isolated antibodies" as used herein refer to antibodies that are substantially physically separated from other cellular material (e.g., separated from cells which produce the antibodies) or from other material that hinders their use either in the diagnostic or therapeutic methods of the invention. Preferably, the isolated antibodies are present in a homogenous population of antibodies (e.g., a population of monoclonal antibodies). Compositions of isolated antibodies can however be combined with other components such as but not limited to pharmaceutically acceptable carriers, adjuvants, and the like.

In one embodiment, the CLIP and HLA peptides useful in the invention are isolated intact soluble monoclonal antibodies specific for CLIP and HLA. As used herein, the term "monoclonal antibody" refers to a homogenous population of immunoglobulins that specifically bind to an identical epitope (i.e., antigenic determinant).

In other embodiments, the peptide is an antibody fragment. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford; and Pier G B, Lyczak J B, Wetzler L M, (eds). Immunology, Infection and Immunity (2004) 1$^{st}$ Ed. American Society for Microbiology Press, Washington D.C.). The pFc' and Fc regions of the antibody, for example, are effectors of the complement cascade and can mediate binding to Fc receptors on phagocytic cells, but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford); and Pier G B, Lyczak J B, Wetzler L M, (eds). Immunology, Infection and Immunity (2004) 1$^{st}$ Ed. American Society for Microbiology Press, Washington D.C.].

The anti-CLIP and HLA antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biot, 2:593-596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

As an alternative to humanization, human antibodies can be generated. A "human antibody" is one which possesses an amino acid sequence which corresponds to that of an antibody produced by a human and/or has been made using any techniques for making human antibodies. This definition of a human antibody specifically excludes a humanized antibody comprising non-human antigen-binding residues. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807.

Human monoclonal antibodies also may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner et al., *J. Immunol.*, 147: 86-95 (1991).

The invention also encompasses the use of single chain variable region fragments (scFv). Single chain variable region fragments are made by linking light and/or heavy chain variable regions by using a short linking peptide. Any peptide having sufficient flexibility and length can be used as a linker in a scFv. Usually the linker is selected to have little to no immunogenicity. An example of a linking peptide is multiple GGGGS residues, which bridge the carboxy terminus of one variable region and the amino terminus of another variable region. Other linker sequences may also be used.

All or any portion of the heavy or light chain can be used in any combination. Typically, the entire variable regions are included in the scFv. For instance, the light chain variable region can be linked to the heavy chain variable region. Alternatively, a portion of the light chain variable region can be linked to the heavy chain variable region, or portion thereof. Also contemplated are scFvs in which the heavy chain variable region is from the antibody of interest, and the light chain variable region is from another immunoglobulin.

The scFvs can be assembled in any order, for example, $V_H$-linker-$V_L$ or $V_L$-linker-$V_H$. There may be a difference in the level of expression of these two configurations in particular expression systems, in which case one of these forms may be preferred. Tandem scFvs can also be made, such as (X)-linker-(X)-linker-(X), in which X are polypeptides form the antibodies of interest, or combinations of these polypeptides with other polypeptides. In another embodiment, single chain antibody polypeptides have no linker polypeptide, or just a short, inflexible linker. Possible configurations are $V_L$-$V_H$ and $V_H$-$V_L$. The linkage is too short to permit interaction between $V_L$ and $V_H$ within the chain, and the chains form homodimers with a $V_L$/$V_H$ antigen binding site at each end. Such molecules are referred to in the art as "diabodies".

Single chain variable regions may be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*, and the expressed protein may be isolated using standard protein purification techniques.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad Sci. USA, 90: 6444-6448 (1993).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Peptides, including antibodies, can be tested for their ability to bind to CLIP and HLA using standard binding assays known in the art. As an example of a suitable assay, CLIP and HLA can be immobilized on a surface (such as in a well of a multi-well plate) and then contacted with a labeled peptide. The amount of peptide that binds to the CLIP and HLA (and thus becomes itself immobilized onto the surface) may then be quantitated to determine whether a particular peptide binds to CLIP and HLA. Alternatively, the amount of peptide not bound to the surface may also be measured. In a variation of this assay, the peptide can be tested for its ability to bind directly to a CLIP and HLA-expressing cell.

The invention also encompasses small molecules that bind to CLIP and HLA. Such binding molecules may be identified by conventional screening methods, such as phage display procedures (e.g. methods described in Hart et al., *J. Biol. Chem.* 269:12468 (1994)). Hart et al. report a filamentous phage display library for identifying novel peptide ligands. In general, phage display libraries using, e.g., M13 or fd phage, are prepared using conventional procedures such as those described in the foregoing reference. The libraries generally display inserts containing from 4 to 80 amino acid residues. The inserts optionally represent a completely degenerate or biased array of peptides. Ligands having the appropriate binding properties are obtained by selecting those phage which express on their surface a ligand that binds to the target molecule. These phage are then subjected to several cycles of reselection to identify the peptide ligand expressing phage that have the most useful binding characteristics. Typically, phage that exhibit the best binding characteristics (e.g., highest affinity) are further characterized by nucleic acid analysis to identify the particular amino acid sequences of the peptide expressed on the phage surface in the optimum length of the express peptide to achieve optimum binding. Phage-display peptide or antibody library is also described in Brissette R et al Curr Opin Drug Discov Devel. 2006 May; 9(3):363-9.

Alternatively, binding molecules can be identified from combinatorial libraries. Many types of combinatorial libraries have been described. For instance, U.S. Pat. Nos. 5,712,171 (which describes methods for constructing arrays of synthetic molecular constructs by forming a plurality of molecular constructs having the scaffold backbone of the chemical molecule and modifying at least one location on the molecule in a logically-ordered array); 5,962,412 (which describes methods for making polymers having specific physiochemical properties); and 5,962,736 (which describes specific arrayed compounds).

Other binding molecules may be identified by those of skill in the art following the guidance described herein. Library technology can be used to identify small molecules, including small peptides, which bind to CLIP and HLA and interrupt its function. One advantage of using libraries for antagonist identification is the facile manipulation of millions of different putative candidates of small size in small reaction volumes (i.e., in synthesis and screening reactions). Another advantage of libraries is the ability to synthesize antagonists which might not otherwise be attainable using naturally occurring sources, particularly in the case of non-peptide moieties.

Small molecule combinatorial libraries may also be generated. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

The CLIP and HLA binding molecules described herein can be used alone or in conjugates with other molecules such as detection or cytotoxic agents in the detection and treatment methods of the invention, as described in more detail herein.

Typically, one of the components usually comprises, or is coupled or conjugated to a detectable label. A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the peptides described herein, or will be able to ascertain such, using routine experimentation. Furthermore, the coupling or conjugation of these labels to the peptides of the invention can be performed using standard techniques common to those of ordinary skill in the art.

Another labeling technique which may result in greater sensitivity consists of coupling the molecules described herein to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Conjugation of the peptides including antibodies or fragments thereof to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$Tl, gamma-emitting radionuclide 99 mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The conjugates also include an antibody conjugated to a cytotoxic agent such as a chemotherapeutic agent, toxin (e.g. an enzymatically active toxin of bacterial, fungal, plant or animal origin, or fragments thereof, or a small molecule toxin), or a radioactive isotope (i.e., a radioconjugate). Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used in the conjugates include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes.

For selective destruction of the cell, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

Additionally the methods of the invention may involve the administration of a glycolytic inhibitor and or a halogenated alky ester. The glycolytic inhibitor and or a halogenated alky ester function as CLIP activity inhibitors that displace CLIP from the MHC on the cell surface. Preferred glycolytic inhibitors are 2-deoxyglucose compounds, defined herein as 2-deoxy-D-glucose, and homologs, analogs, and/or derivatives of 2-deoxy-D-glucose. While the levo form is not prevalent, and 2-deoxy-D-glucose is preferred, the term "2-deoxyglucose" is intended to cover inter alia either 2-deoxy-D-glucose and 2-deoxy-L-glucose, or a mixture thereof.

Examples of 2-deoxyglucose compounds useful in the invention are: 2-deoxy-D-glucose, 2-deoxy-L-glucose; 2-bromo-D-glucose, 2-fluoro-D-glucose, 2-iodo-D-glucose, 6-fluoro-D-glucose, 6-thio-D-glucose, 7-glucosyl fluoride, 3-fluoro-D-glucose, 4-fluoro-D-glucose, 1-O-propyl ester of 2-deoxy-D-glucose, 1-O-tridecyl ester of 2-deoxy-D-glucose, 1-O-pentadecyl ester of 2-deoxy-D-glucose, 3-O-propyl ester of 2-deoxy-D-glucose, 3-O-tridecyl ester of 2-deoxy-D-glucose, 3-O-pentadecyl ester of 2-deoxy-D-glucose, 4-O-propyl ester of 2-deoxy-D-glucose, 4-O-tridecyl ester of 2-deoxy-D-glucose, 4-O-pentadecyl ester of 2-deoxy-D-glucose, 6-O-propyl ester of 2-deoxy-D-glucose, 6-O-tridecyl ester of 2-deoxy-D-glucose, 6-O-pentadecyl ester of 2-deoxy-D-glucose, and 5-thio-D-glucose, and mixtures thereof.

Glycolytic inhibitors particularly useful herein can have the formula:

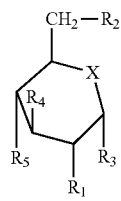

wherein: X represents an O or S atom; $R_1$ represents a hydrogen atom or a halogen atom; $R_2$ represents a hydroxyl group, a halogen atom, a thiol group, or CO—$R_6$; and $R_3$, $R_4$, and $R_5$ each represent a hydroxyl group, a halogen atom, or CO—$R_6$ wherein $R_6$ represents an alkyl group of from 1 to 20 carbon atoms, and wherein at least two of $R_3$, $R_4$, and $R_5$ are hydroxyl groups. The halogen atom is preferably F, and $R_6$ is preferably a $C_3$-$C_{15}$ alkyl group. A preferred glycolytic inhibitor is 2-deoxy-D-glucose. Such glycolytic inhibitors are described in detail in application Ser. No. 10/866,541, filed Jun. 11, 2004, by M. K. Newell et al., the disclosure of which is incorporated herein by reference.

In some embodiments of the invention, one can remove CLIP by administering as a pharmacon a combination of a glycolytic inhibitor and a halogenated alky ester. The combination is preferably combined as a single bifunctional compound acting as a prodrug, which is hydrolyzed by one or more physiologically available eterases. Because of the overall availability of the various esterases in physiological conditions, one can form an ester by combining the glycolytic inhibitor and the halogenated alkyl ester. The prodrug will be hydrolyzed by a physiologically available esterase into its two functional form.

In other particular embodiments, the halogenated alkyl ester has the formula: $R^7{}_m CH_{1-m} X_2 R^8{}_n COOY$ where $R^7$ is methyl, ethyl, propyl or butyl, m and n are each is 0 or 1, $R^8$ is CH or CHCH, X is a halogen, for example independently selected from chlorine, bromine, iodine and fluorine. When used as a separate compound, Y is an alkali metal or alkaline earth metal ion such as sodium, potassium, calcium, and magnesium, ammonium, and substituted ammonium where the substituent is a mono- or di-lower alkyl radical of 1-4 carbon atoms and ethylene diammonium. When used combined with the glycolytic inhibitor as a prodrug, Y is esterified with the glycolytic inhibitor as described in the Methods and Materials section below.

Preferred prodrugs are those prepared by esterification of dichloroacetic acid, exemplified by the following structures:

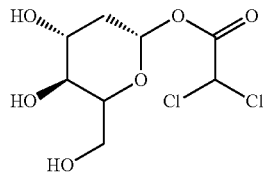

(2S,4R,5S)-4,5-dihydroxy-6-(hydroxymethyl)tetrahydro-2H-pyran-2-yl dichloroacetate

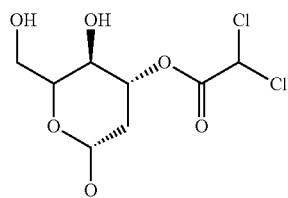

(3S,4R,6R)-3,6-dihydroxy-2-(hydroxymethyl)tetrahydro-2H-pyran-4-yl dichloroacetate

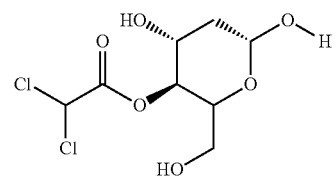

(3S,4R,6R)-4,6-dihydroxy-2-(hydroxymethyl)tetrahydro-2H-pyran-3-yl dichloroacetate

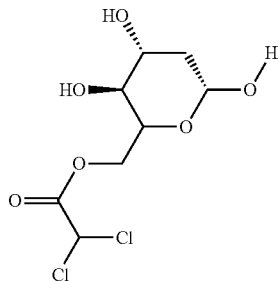

[(3S,4R,6R)-3,4,6-trihydroxytetrahydro-2H-pyran-2-yl]methyl dichloroacetate

In certain embodiments, the method for treating a subject involves administering to the subject an effective amount of a nucleic acid molecule to treat the disorder. In certain of these embodiments, the method for treatment involves administering to the subject an effective amount of a small interfering nucleic acid molecule such as antisense, RNAi, or siRNA oligonucleotide to reduce the level of CLIP molecule, HLA-DO, or HLA-DM expression. The nucleotide sequences of CLIP molecules, HLA-DO, and HLA-DM are all well known in the art and can be used by one of skill in the art using art recognized techniques in combination with the guidance set forth below to produce the appropriate siRNA molecules. Such methods are described in more detail below.

The invention features the use of small nucleic acid molecules, referred to as small interfering nucleic acid (siNA) that include, for example: microRNA (miRNA), small interfering RNA (siRNA), double-stranded RNA (dsRNA), and short hairpin RNA (shRNA) molecules. An siNA of the invention can be unmodified or chemically-modified. An siNA of the instant invention can be chemically synthesized, expressed from a vector or enzymatically synthesized as discussed herein. The instant invention also features various chemically-modified synthetic small interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic applications.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'amino, 2'-C-allyl, 2'-fluoro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314317; Usman and Cedergren, Trends in Biochem. Sci., 1992, 17, 334 339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., molecule comprises one or more chemical modifications.

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In some embodiments, a small interfering nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the a-fetoprotein promoter.

As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. An expression vector is one into which a desired DNA sequence may be inserted by restriction and ligation such that it is operably joined to regulatory sequences and may be expressed as an RNA transcript. In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., Virology 219:220-227, 1996; Eloit et al., J. Virol. 7:5375-5381, 1997; Chengalvala et al., Vaccine 15:335-339, 1997), a modified retrovirus (Townsend et al., J. Virol. 71:3365-3374, 1997), a nonreplicating retrovirus (Irwin et al., J. Virol. 68:5036-5044, 1994), a replication defective Semliki Forest virus (Zhao et al., Proc. Natl. Acad. Sci. USA 92:3009-3013, 1995), canarypox virus and highly attenuated vaccinia virus derivative (Paoletti, Proc. Natl. Acad. Sci. USA 93:11349-11353, 1996), non-replicative vaccinia virus (Moss, Proc. Natl. Acad. Sci. USA 93:11341-11348, 1996), replicative vaccinia virus (Moss, Dev. Biol. Stand. 82:55-63, 1994), Venzuelan equine encephalitis virus (Davis et al., J. Virol. 70:3781-3787, 1996), Sindbis virus (Pugachev et al., Virology 212:587-594, 1995), and Ty virus-like particle (Allsopp et al., Eur. J. Immunol 26:1951-1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, N.J. (1991).

Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. For certain uses, it is preferred to target the nucleic acid molecule (e.g., an small interfering nucleic acid molecule) to particular cells. In such instances, a vehicle used for delivering a nucleic acid molecule of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid molecule delivery vehicle. Especially preferred are monoclonal antibodies. Where liposomes are employed to deliver the nucleic acid molecules of the invention, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

In addition to delivery through the use of vectors, nucleic acids of the invention may be delivered to cells without vectors, e.g., as "naked" nucleic acid delivery using methods known to those of skill in the art.

Other inhibitor molecules that can be used include ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat Med. 4(8):967-71, 1998). For example, neoplastic reversion was obtained using a ribozyme targeted to an H-Ras mutation in bladder carcinoma cells (Feng et al., Cancer Res. 55(10):2024-8, 1995).

Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6): 643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4):307-17, 1991; Knudsen and Nielson Nucleic Acids Res. 24(3):494-500, 1996; Taylor et al., Arch. Surg. 132(11):1177-83, 1997). Minor-groove binding polyamides can bind in a sequence-specific manner to DNA targets and hence may represent useful small molecules for future suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have led to a reduction in RNA levels without a concomitant reduction in proteins, whereas in others, reductions in RNA have been mirrored by reductions in protein.

The diverse array of suppression strategies that can be employed includes the use of DNA and/or RNA aptamers that can be selected to target, for example CLIP or HLA-DO. Suppression and replacement using aptamers for suppression in conjunction with a modified replacement gene and encoded protein that is refractory or partially refractory to aptamer-based suppression could be used in the invention.

The active agents of the invention are administered to the subject in an effective amount for treating disorders such as autoimmune disease, cancer, HIV infection, other infections, and graft rejection. An "effective amount", for instance, is an amount necessary or sufficient to realize a desired biologic effect. An "effective amount for treating cancer", for instance, is an effective amount of a compound of the invention could be that amount necessary to (i) kill a cancer cell; (ii) inhibit the further growth of the cancer, i.e., arresting or slowing its development; and/or (iii) sensitize a cancer cell to an anti-cancer agent or therapeutic. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or absolute elimination of symptoms resulting from the disease. In another embodiment, the biological effect is the complete abrogation of the disease, as evidenced for example, by the absence of a symptom of the disease. or a tumor or a biopsy or blood smear which is free of cancer cells.

The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Pharmaceutical compositions of the present invention comprise an effective amount of one or agent, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The agent may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 0.1 µg to 20 mg/kg/day, more typically from about 1 to 10 mg/kg/day, and most typically from about 1 to 5 mg/kg/day. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with a cancer medicament a sub-therapeutic dosage of either the molecules or the cancer medicament, or a sub-therapeutic dosage of both, is used in the treatment of a subject having, or at risk of developing, cancer. When the two classes of drugs are used together, the cancer medicament may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a cancer medicament is one which would not produce the desired therapeutic result in the subject in the absence of the administration of the molecules of the invention. Therapeutic doses of cancer medicaments are well known in the field of medicine for the treatment of cancer. These dosages have been extensively described in references such as Remington's Pharmaceutical Sciences, 18th ed., 1990; as well as many other medical references relied upon by the medical profession as guidance for the treatment of cancer. Therapeutic dosages of antibodies have also been described in the art.

A variety of administration routes are available. The particular mode selected will depend, of course, upon the particular active agents selected, the particular condition being treated and the dosage required for therapeutic efficacy. The methods of this invention, generally speaking, may be practiced using any mode of administration that is medically acceptable, meaning any mode that produces effective levels of protection without causing clinically unacceptable adverse effects. Preferred modes of administration are parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the invention can be administered by any ordinary route for administering medications. Depending upon the type of cancer to be treated, compounds of the invention may be inhaled, ingested or administered by systemic routes. Systemic routes include oral and parenteral. Inhaled medications are preferred in some embodiments because of the direct delivery to the lung, particularly in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Preferred routes of administration include but are not limited to oral, parenteral, intramuscular, intranasal, intratracheal, intrathecal, intravenous, inhalation, ocular, vaginal, and rectal. For use in therapy, an effective amount of the compounds of the invention can be administered to a subject by any mode that delivers the nucleic acid to the affected organ or tissue. "Administering" the pharmaceutical composition of the present invention may be accomplished by any means known to the skilled artisan.

According to the methods of the invention, the compound may be administered in a pharmaceutical composition. In general, a pharmaceutical composition comprises the compound of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients, e.g., the ability of the peptide to bind to CLIP and HLA.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in *Remington's Pharmaceutical Sciences,* 18th edition, 1990, pp 1694-1712; incorporated by reference). Those of skill in the art can readily determine the various parameters and conditions for producing aerosols without resort to undue experimentation.

The compounds of the invention may be administered directly to a tissue. Preferably, the tissue is one in which the CLIP expressing cells are found. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application serial no. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic diseases or recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Therapeutic formulations of the peptides or antibodies may be prepared for storage by mixing a peptide or antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

B-Cell Apoptosis after Coxsackievirus Infection

During the course of Coxsackievirus infection, animals that recover from the virus without subsequent autoimmune sequelae have high percentages of splenic B cell apoptosis during the infection in vivo (FIG. 1). Those animals susceptible to Coxsackievirus-mediated autoimmune disease have non-specifically activated B cells that do not undergo apoptosis, at least not during acute infection, nor during the time period prior to autoimmune symptoms indicating that a common feature in the development of autoimmune disease is failure of non-specifically activated B cells to die.

Example 2

Activated B Cells in HIV Disease Mediate NK Cell Activation

Figure 2A:
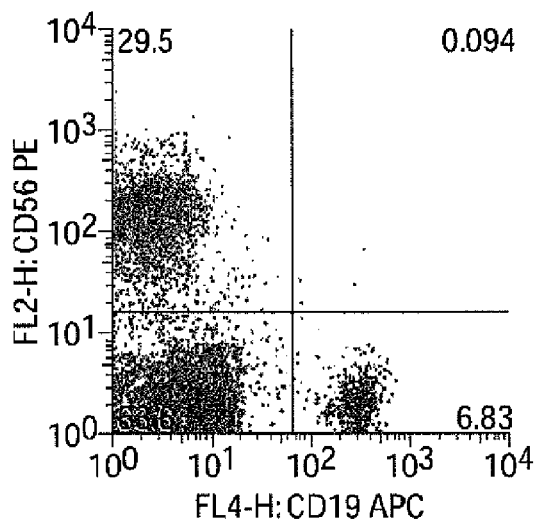
FIGS. 2A and 2B are dot plots representing flow cytometric analysis of 5 day cultures in which CD40 Ligand activated B cells were co-cultured with autologous PMBCs for 5 days.
Figure 2B:
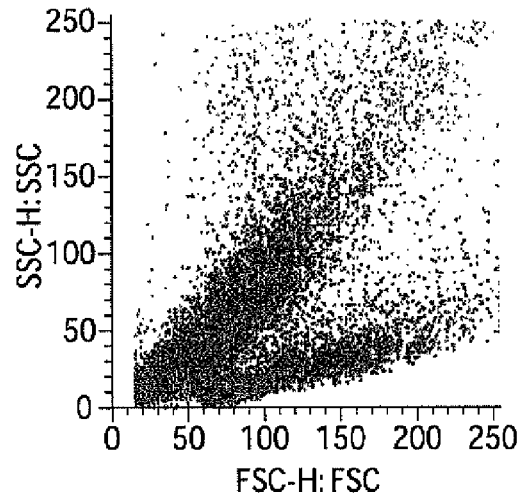
Figures 1, 3A:
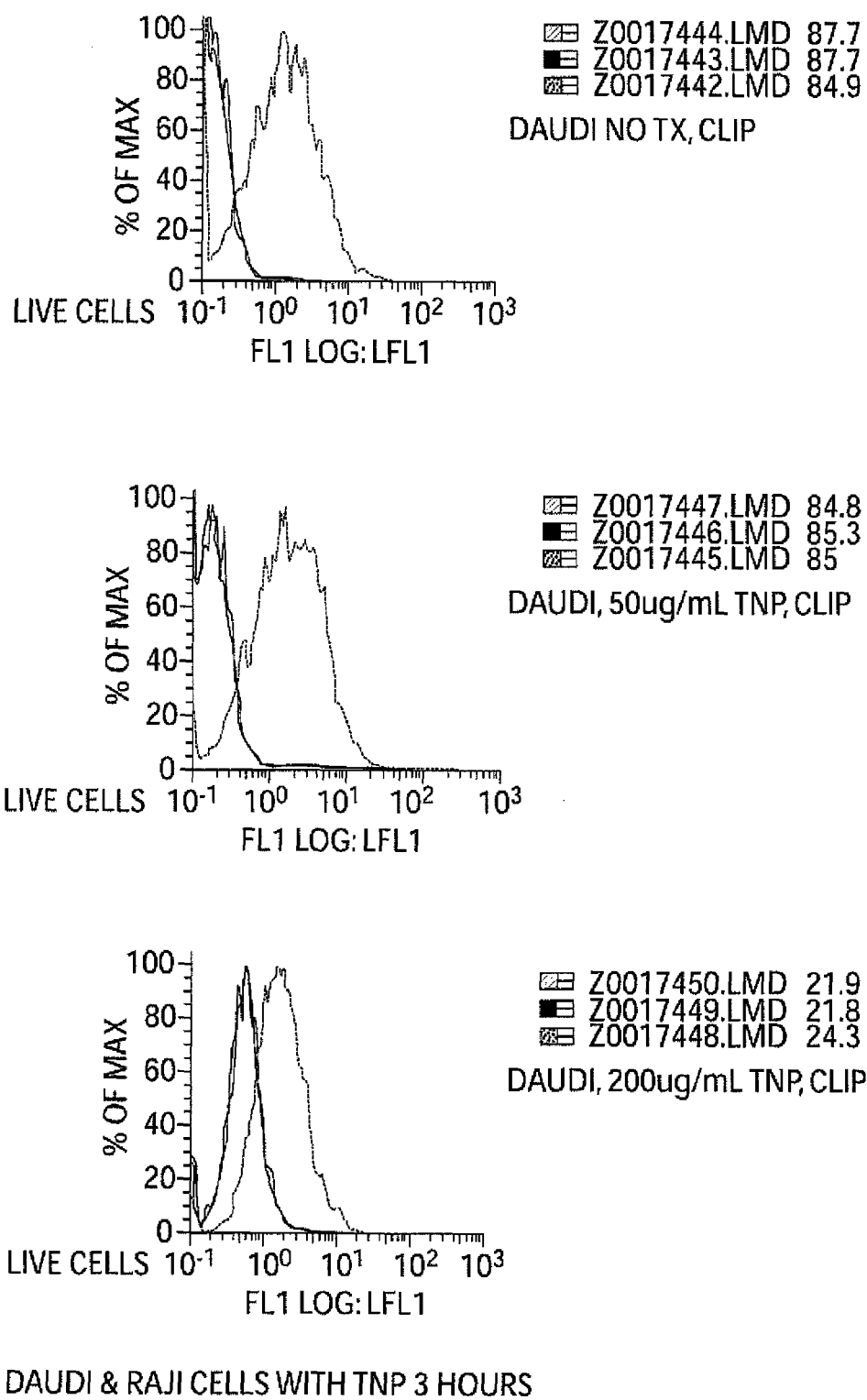
FIG. 3A is a 3 hour reaction.
Figures 2, 3A:
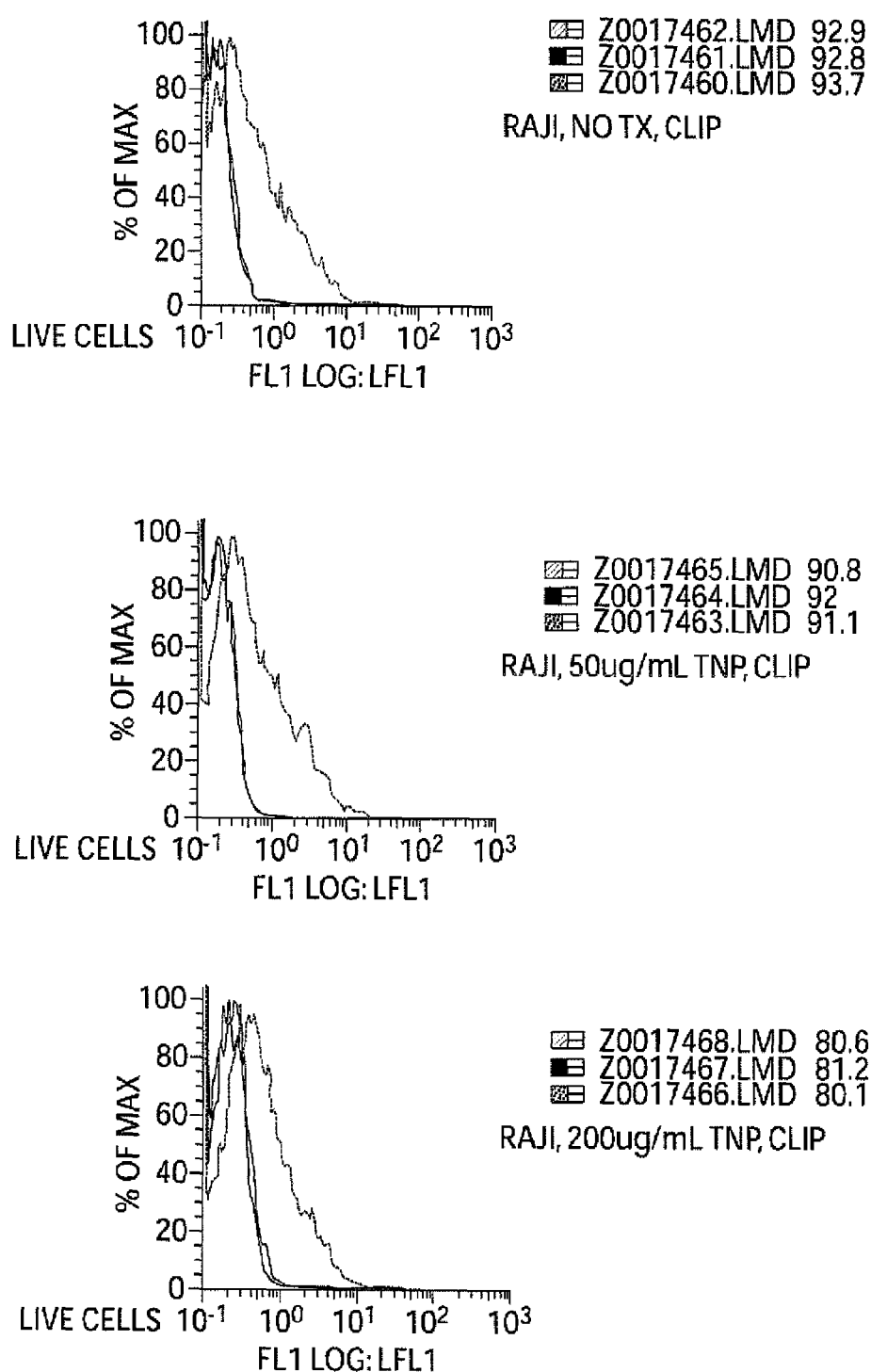
Figures 1, 3B:
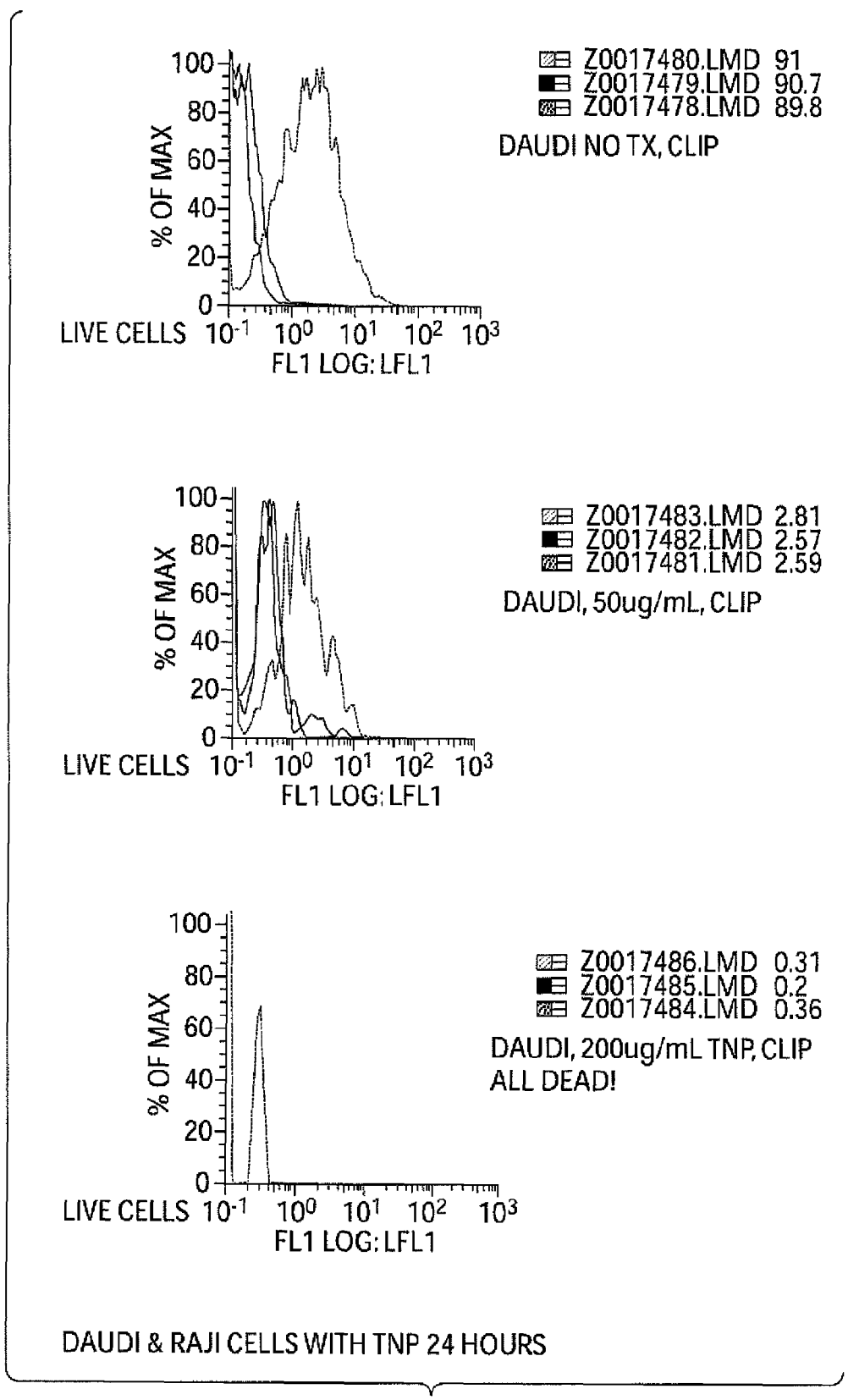
FIG. 3B is a 24 hour reaction.
Figures 2, 3B:
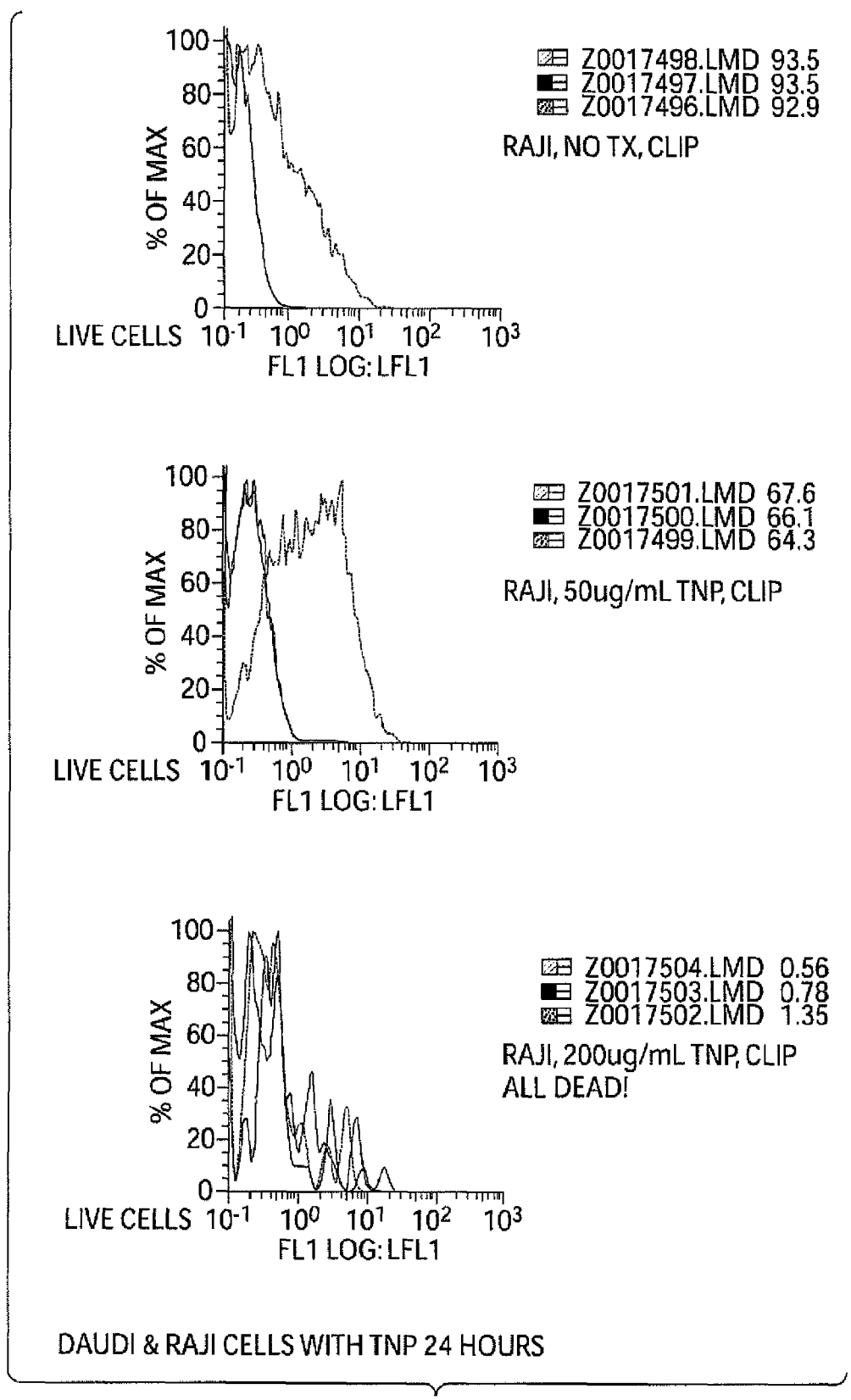
Figure 3C:
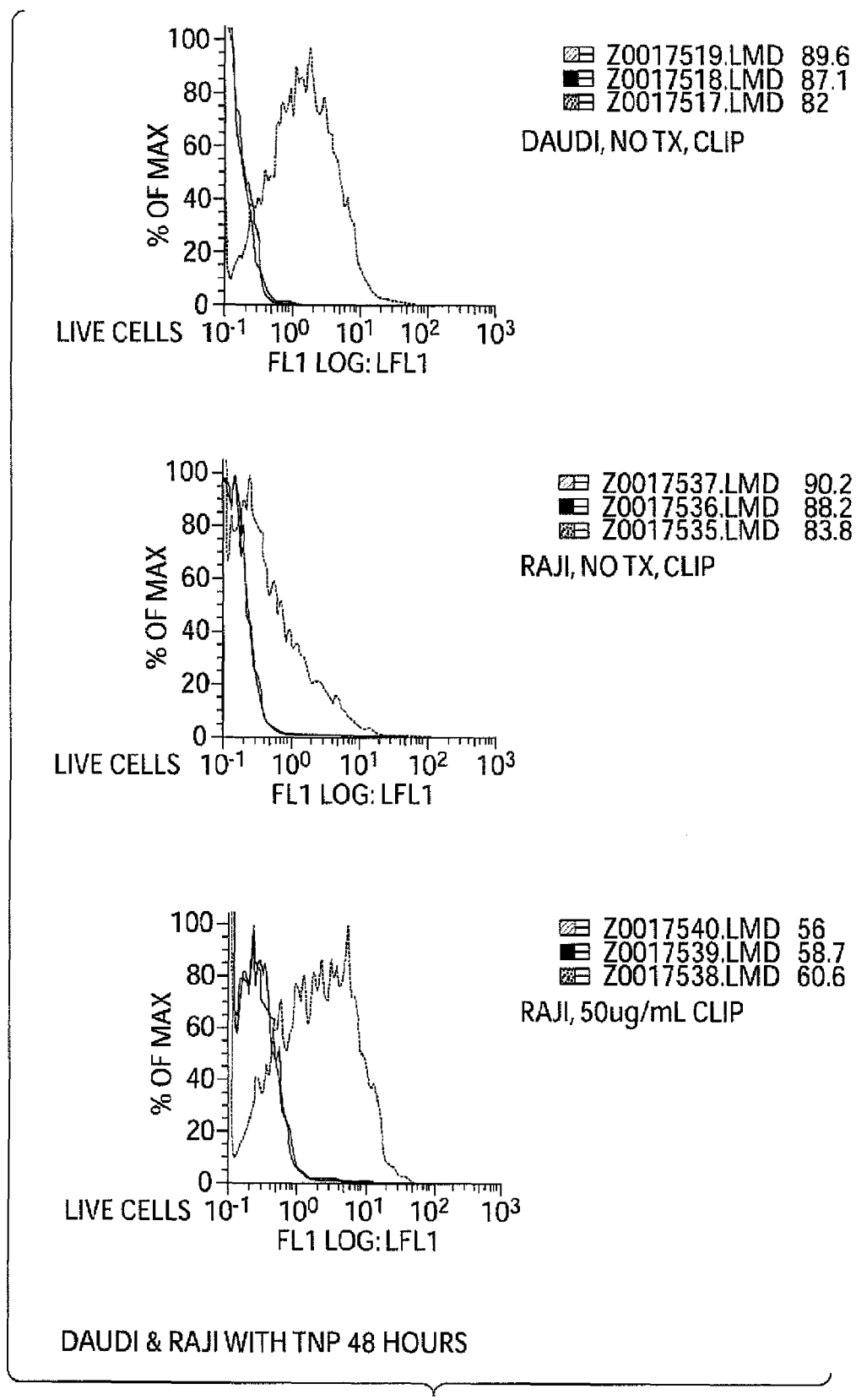
FIG. 3C is a 48 hour reaction.

We experimentally induced polyclonal activation of peripheral blood human B cells in an antigen-independent fashion using a combination of CD40 engagement (CD40Ligand bearing fibroblasts) and culture in recombinant IL-4. We isolated the activated B cells and return them to co-culture with autologous peripheral blood mononuclear cells (PBMCs). After five days of co-culture, we observed a striking increase in the percentage of activated NK cells in the PBMC culture (NK cells accounting for up to 25-50%, FIG. 2a, of the surviving PBMCs), and a dramatic apoptotic loss of the activated B cells (FIG. 2b). These data indicate that antigen-independent activated B cells in HIV disease initially activate NK cells.

Example 3

Antigen-Independent B Cell Activation Results in NK Cell Activity

Elements of HIV infection that provide an antigen-independent activation signal to B cells that results in NK cell activation and polyclonal B cell activation are examined.

Antigen-independent activation of B cells: Human B cells: PBMCs are prepared from 5 normal and 5 HIV-infected adult donors using standard Ficoll-Hypaque density-gradient techniques. Irradiated (75 Gy) human CD40L-transfected murine fibroblasts (LTK-CD40L), are plated in six-well plates (BD Bioscience, Franklin Lakes, N.J.) at a concentration of 0.1× 106 cells/well, in RPMI complete medium and cultured overnight at 37° C., 5% $CO_2$. After washing twice with PBS, 2×106 cells/mL PBMC are co-cultured with LTK-CD40L cells in the presence of recombinant human interleukin-4 (rhIL-4; 4 ng/mL; Peprotech, Rocky Hill, N.J.) or with purified HIV derived gp 120 protein in complete Dulbecco's medium (Invitrogen), supplemented with 10% human AB serum (Gemini Bio-Product, Woodland, Calif.) Cultured cells are transferred to new plates with freshly prepared, irradiated LTK-CD40L cells every 3 to 5 days. Before use, dead cells are removed from the CD40-B cells by Ficoll density centrifugation, followed by washing twice with PBS. The viability of this fraction is expected to be >99%, and >95% of the cells, using this protocol, have been shown to be B cells that are more than 95% pure CD19+ and CD20+ after 2 weeks of culture. This protocol yields a viability of >99%, and >95% of the cells have been shown to be B cells that are more than 95% pure CD19+ and CD20+ after 2 weeks of culture.

The activated B cells are co-cultured with autologous PBMC at a ratio of 1:10 and cultured for five days. Harvested cells are stained with fluorochrome-conjugated antibodies (BD Pharmingen) to CD56, CD3, CD19, CD4, and CD8. Cells are analyzed flow cytometrically to determine the percentage of NK cells (Percent CD56+, CD3−) resulting from co-culture comparing non-infected to infected samples. NK cells are counter-stained for NK killing ligand KIR3DS1, NKG2D, FaL, or PD1. Similarly the percent surviving large and small C19+ cells are quantitated flow cytometrically.

B cell activation in HIV: To determine if activated NK or CD3 T cells promote polyclonal B cell activation, we perform reciprocal co-culture experiments in which we purposely activate NKs or CD3+ T cells and co-culture 1:10 in PBMC from the autologous donors. PBMCs are prepared from HIV infected or uninfected adult donors using standard Ficoll-Hypaque density-gradient techniques. To activate NKs and CD3+ T cells, PBMCs are cultured in RPMI with 10% FCS, 1 mM penicillin, 1 mM Glutamax, and 1% W/V glucose at 2.0-4.0×106/mL for 3 days with 1:40,000 OKT3, 100 U/mL IL-2, or no stimulation (resting). After 3 days stimulation, non-adherent PBMCs are gently harvested and immune cell subsets are purified by MACS technology according to manufacturers protocol (Miltenyi Biotec, Auburn Calif.). In brief, NK cells are first selected using the CD56+multisort kit, followed by bead release, and depletion with anti-CD3 beads. T cells are obtained by depleting non-adherent PBMCs with CD56 beads with or without anti-CD4 or anti-CD8 beads for isolation of each individual subset. Purity of cell fractions are confirmed for each experiment by flow cytometry using CD56, CD3, CD4, CD8 and CD14 antibodies. Following culture for 5 days, we use flow cytometry to determine relative changes in CD19+, CD4, CD8, NK, CD3, and CD69 as a marker for activation.

We examine the NK cells from the co-culture experiments for KIR3DS1 and other killer cell ligands including NKG2D ligand, PD1, and FasL that are indicative of killer cell functions.

Antigen-independent activation of mouse B cells. Mouse spleens are removed from C57B16 mice, red cells are removed using buffered ammonium chloride, T cells are depleted with an anti-T cell antibody cocktail (HO13, GK1.5 and 30H12) and complement. T depleted splenocytes are washed and fractionated using Percoll density gradient centrifugation. We isolate the B cells at the 1.079/1.085 g/ml density interface (resting B cells) and wash to remove residual Percoll. The cells are cultured in the presence of LPS or tri-palmitoyl-S-glyceryl-cysteinyl N-terminus (Pam(3)Cys), agonists of TLR2, on B cells. The activated B cells are co-cultured with total spleen cells at a ratio of 1:10 B cell:total spleen cells. After five days in culture, the remaining cells are analyzed for expansion of cell subsets including those expressing mouse CD56, CD3, B220, CD4 and CD8. These cell surface molecules are analyzed flow cytometrically. CD56+CD3− cells are counterstained for NKG2D and other death-inducing receptors.

Example 4

NK Cells Kill Activated CD4+ T Cells

The ability of NK cells to lyse activated CD4 T cells as targets as a result of NK cell activation and changes in the CD4 T cell target is examined.

Activation of Human NK and CD3+ T cells: PBMCs are prepared from HIV infected or uninfected adult donors using standard Ficoll-Hypaque density-gradient techniques. NKs and CD3+ T cells are activated and isolated as disclosed herein. T cells and NK cells are routinely between 80-95% pure with less than 1% monocyte contamination. T cell activation in OKT3-stimulated PBMCs is confirmed by assays using 3H-thymidine incorporation. NK cell activation is confirmed by increase in size and granularity by flow cytometry, by staining for CD56+ and CD3− fow cytometrically, and by lytic activity as measured by chromium release of well-established NK targets. We load well-established NK cell targets or the non-specifically activated B cells as disclosed herein with 51-Chromium. We use chromium release as a measurement of target cell death.

Activation of mouse NK and CD3+ T cells: We isolate splenocytes as disclosed herein. The red blood cell-depleted spleen cells are cultured in recombinant mouse IL-2 or with 145.2C11 (anti-mouse CD3, Pharmingen) for 3 days. After stimulation, the cells are harvested and purified using Cell-ect Isolation kits for either NK, CD4, or CD8+ T cells. The cells are then co-cultured with 51-Chromium-labelled, well-established NK cell targets or with 51-Chromium-labelled non-specifically activated B cells as disclosed herein.

Example 5

Chronically Activated HIV Infected (or HIV-Specific CD4 T Cells) are the Intercellular Targets of Activated Killer Cells Chronically activated CD4+ T cells become particularly susceptible to killer cells as a consequence of the chronic immune stimulation resulting from HIV infection.

We isolate NK cells from uninfected or HIV-infected individuals using the CD56+multisort kit as disclosed herein. We activate the cells in IL-2 as disclosed herein. We perform co-culture experiments with these cells added back to PBMC at a 1:10 ratio from autologous donors. Prior to co-culture we examine the NK cells from HIV infected and uninfected donors for deat-inducing receptor: ligand pairs killer, including KIR3DS1, FasL, and NKG2D ligands that are indicative of killer cell functions. In parallel, we stain pre- and post-coculture PBMCs from the autologous donors of HIV infected or uninfected donors.

Example 6

TNP MIXTURE Displaces Clip from Model B Cell Lines

Kinetics of CLIP displacement from the surface of model B cells lines (Daudi and Raji) in response to thymic nuclear protein mixture was determined.

Results were expressed in histogram analyses (FIG. 3). The Y axis represents cell number of the 5000 live cells versus the X axis which is a reflection of relative Fitc fluorescence. The distance between the histogram from the isotype control staining versus the histogram reflecting the specific stain is a measure of level of cell surface CLIP on a population of live Raji or Daudi cells as indicated.

At three hours, on both cell lines, we see evidence by diminished ratio of Isotype to CLIP staining, that the TNP mixtures at 200 microgram/ml cause a reduction in detectable cell surface CLIP.

At 24 hours, the effect was less, and may have caused an increase in detectable CLIP. Noticeably at 24 hours, the TNP mixture caused death of the B cell lines at the 200 microgram/mL concentrations and by 48 hours all of the cells treated with 200 micrograms were dead and the 50 microgram concentrations also resulted in significant toxicity.

At 3 hours, treatment with 200 micrograms TNP/ml, there was 2.5 times the number of dead cells as determined by Trypan blue exclusion. Cell death in the flow cytometric experiments was, determined by forward versus side scatter changes (decreased forward scatter, increased side scatter).

Materials and Methods

Cell Culture Conditions: The Raji and Daudi cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

Protocol: Cells were plated into a 12 well plate with 3 mls total volume containing approximately $0.5 \times 10^6$/well for Daudi cells and $1.0 \times 10^6$/well for Raji cells. Treatment groups included no treatment as control; 50 micrograms/ml TNP mixture; 200-micrograms/ml TNP mixture; 50 micrograms of control bovine albumin; or 200 micrograms/ml bovine albumin as protein controls.

The cells were incubated at 37° C. in an atmosphere containing 5% $CO_2$ and approximately 92% humidity. The cells were incubated for 3, 24, and 48 hours. At each time point, the cells from that experimental time were harvested and stained for flow cytometric analysis of cell surface expression of CLIP (MHC Class II invariant peptide, human) by using the commercially available (Becton/Dickinson/PHarmingen) anti-human CLIP Fitc. Catalogue #555981.

Harvested cells were stained using standard staining procedure that called for a 1:100 dilution of Fitc-anti-human CLIP or isotype control. Following staining on ice for 25 minutes, cells were washed with PBS/FCS and resuspended in 100 microliters and added to staining tubes containing 400 microliters of PBS. Samples were acquired and analyzed on a Coulter Excel Flow Cytometer.

Example 7

MKN1 (bioCLIP) Alters Cell Surface Clip and CD74 Levels

The ability of MKN1 (bioCLIP) to alter cell surface CLIP and CD74 levels was determined using Raji or Daudi cells.

Data were analyzed by histogram with Y axis represents cell number of the 5000 live cells versus the X axis which is a reflection of relative FITC fluorescence with either antibodies to CLIP or CD74. The distance between the histogram from the isotype control staining versus the histogram reflecting the specific stain and is a measure of level of cell surface CLIP or CD74 when staining a population of live Raji or Daudi cells.

Our results show that treatment with MKN1 (bioCLIP) alters cell surface CLIP and CD74 levels.

Materials and Methods:

Cell Culture Conditions: The Raji and Daudi cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

Protocol: Cells were plated into a 12 well plate with 3 mls total volume containing approximately $0.5 \times 10^6$/mL for Daudi cells and $0.5 \times 10^6$/mL for Raji cells. Treatment groups included no treatment as control; MKN 3 and MKN 5 at 50 microMolar final concentration based on the reported molarity of the synthesized compounds.

Peptide 1: MKN.1 (19 mer) Biotin at N-Terminal=Biotinylated CLIP

SGG GSK MRM ATP LLM QAL Y (SEQ ID NO. 5)

5-10 mg Obtained @>95% purity (ELIM Pharmaceuticals)

The cells were incubated at 37° C. in an atmosphere containing 5% $CO_2$ and approximately 92% humidity. The cells were incubated for 24 and 48 hours. At each time point, the cells from that experimental time were harvested and stained for flow cytometric analysis of cell surface expression of CLIP (MHC Class II invariant peptide, human) by using the commercially available (Becton/Dickinson/Pharmingen) anti-human CLIP Fitc. Catalogue #555981 versus Streptavidin and for CD74 using the commercially available (Becton/Dickinson/Pharmingen) anti-human CC74 Fitc antibody.

Harvested cells were stained using standard staining procedure that called for a 1:100 dilution of Fitc-anti-human CLIP or CD74 antibody (Fitc, Pharmingen, Cat #554647) or isotype control. Following staining on ice for 25 minutes, cells were washed with PBS/FCS and resuspended in 100 microliters and added to staining tubes containing 400 microliters of PBS. Samples were acquired and analyzed on a Coulter Excel Flow Cytometer.

Example 8

2-Deoxyglucose and Dichloroacetate Cause Removal of B Cell Surface CLIP

The ability of 2-Deoxyglucose and dichloroacetate affect B cell surface CLIP was determined.

Figure 4:
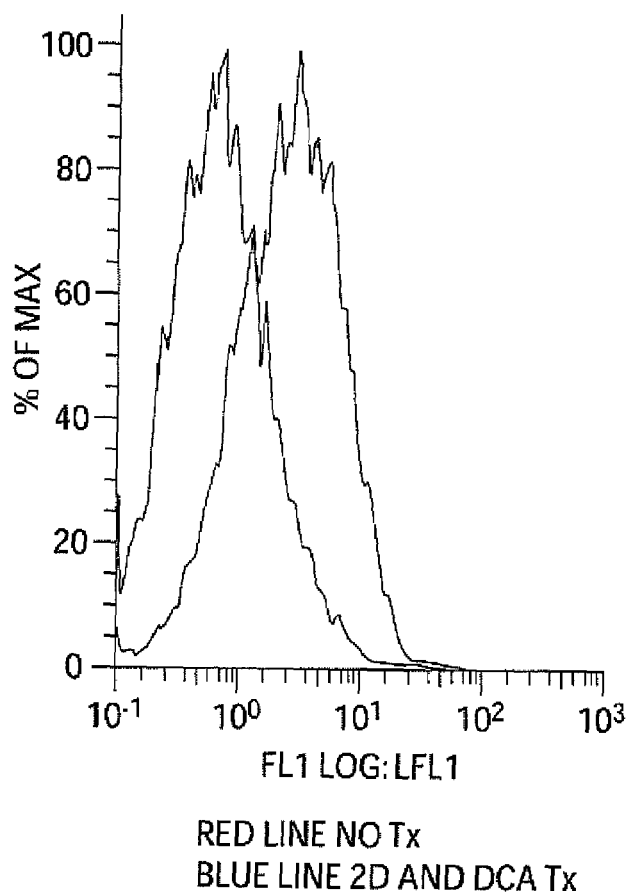
FIG. 4 depicts that 2-Deoxyglucose and dichloroacetate affects B cell surface CLIP.

Results are expressed in histogram analyses (FIG. 4). The Y axis represents cell number of the 5000 live cells versus the X axis which is a reflection of relative Fitc fluorescence with either antibodies to CLIP. The distance between the histogram from the isotype control staining versus the histogram reflecting the specific stain and is a measure of level of cell surface CLIP when staining a population of live Raji or Daudi cells as indicated.

Our results show that treatment equimolar amounts of 2-deoxyglucose and dichloroacetate decrease (remove) cell surface CLIP from both B cell lines optimally at 48 hours.

Materials and Methods

Cell Culture Conditions: The Raji and Daudi cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

Protocol: Cells were plated into a 12 well plate with 3 mls total volume containing approximately $0.5 \times 10^6$/ml for Daudi cells and $0.5 \times 10^6$/ml for Raji cells. Treatment groups included no treatment as control; MKN 3 and MKN 5 at 50 microMolar final concentration based on the reported molarity of the synthesized compounds.

The cells were incubated at 37° C. in an atmosphere containing 5% $CO_2$ and approximately 92% humidity. The cells were incubated for 4, 24 and 48 hours with or without 2 deoxyglucose and dichloroacetate at 1 mg/ml of each compound. At each time point, the cells from that experimental time were harvested and stained for flow cytometric analysis of cell surface expression of CLIP (MHC Class II invariant peptide, human) by using the commercially available (Becton/Dickinson/PHarmingen) anti-human CLIP Fitc. Catalogue #555981.

Harvested cells were stained using standard staining procedure that called for a 1:100 dilution of Fitc-anti-human CLIP (Fitc, Pharmingen, Cat #555981) or isotype control. Following staining on ice for 25 minutes, cells were washed with PBS/FCS and resuspended in 100 microliters and added to staining tubes containing 400 microliters of PBS. Samples were acquired and analyzed on a Coulter Excel Flow Cytometer.

Example 9

Competing Peptides Induce Cell Surface Expression of CD1d

The ability of synthetic peptides to compete with binding of CLIP peptides and result in the cell surface expression of CD1d was determined.

Figure 5:
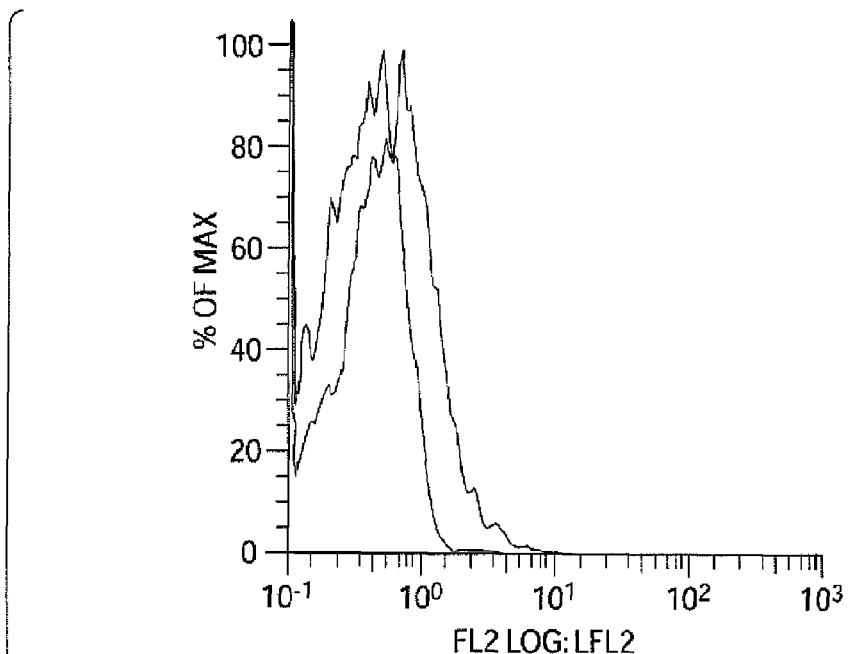
FIG. 5 depicts CLIP displacement from the surface of model B cells lines (Daudi and Raji) in response to a synthetic peptide FRIMAVLAS (SEQ ID NO. 2).
Figure 5:
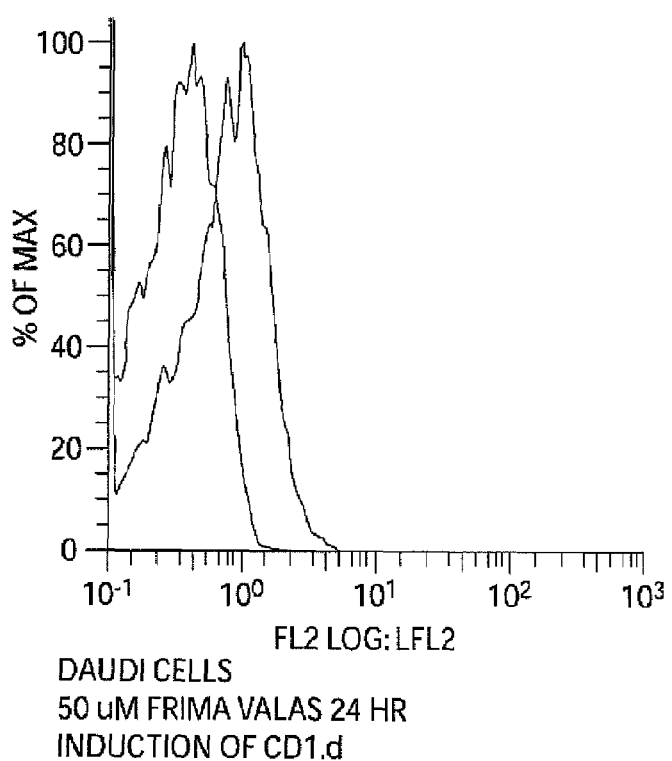
Figure 4:
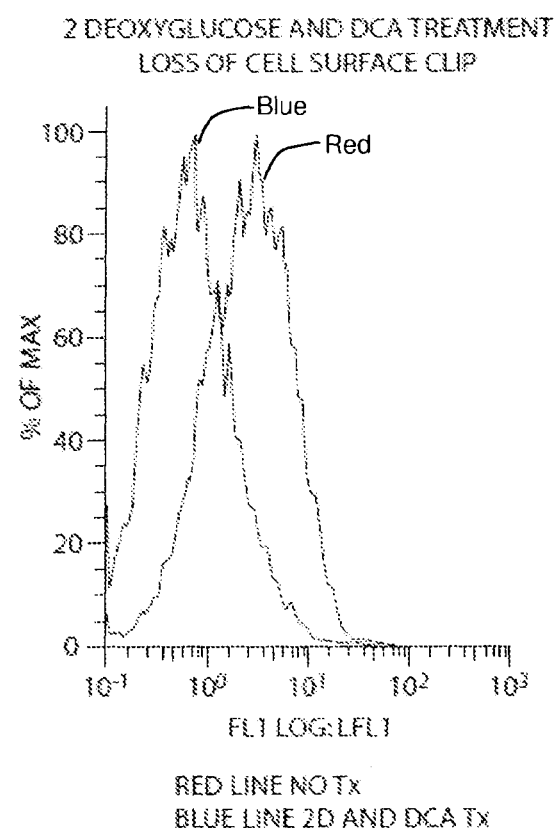
Figure 5:
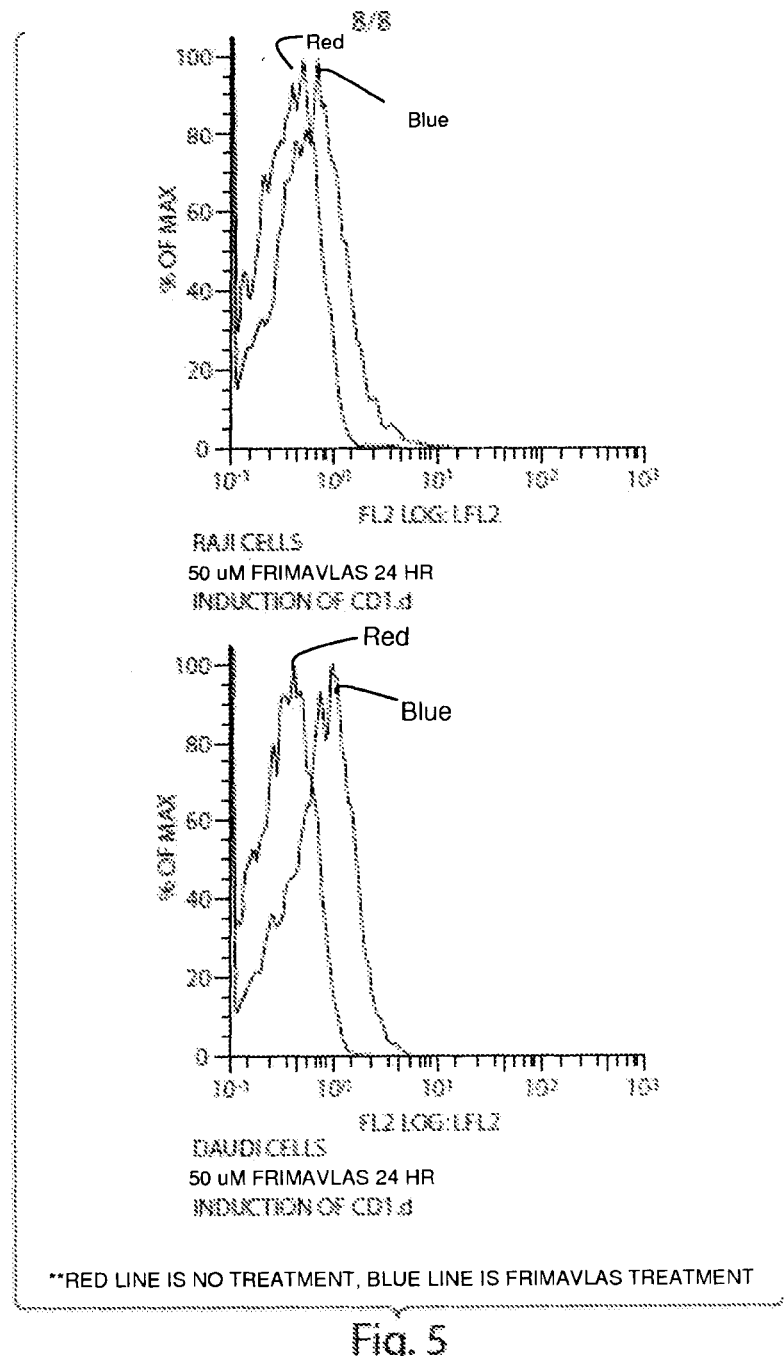

Results: The results shown in FIG. 5 are expressed in histogram analyses. The Y axis represents cell number of the 5000 live cells versus the X axis which is a reflection of relative Fitc fluorescence versus Streptavidin-PE (eBioscience, Cat. #12-4317) that will bind with high affinity to cell-bound biotinylated peptides. The distance between the histogram from the isotype control staining versus the histogram reflecting the specific stain and is a measure of level of cell surface CD1d.

At four hours, on both cell lines, significant evidence that the biotinylated synthetic peptide bound with high affinity to the human B cell lines, Raji and Daudi, at 4 hours was observed. Less binding is observed at 24 hours. The cells were counter-stained the cells with FITC-Anti-CD1d and found that treatment and binding of Biotinylated FRIMAVLAS (SEQ ID NO. 2) resulted in cell surface expression of CD1d on both cell lines, marginally at 4 hours and slightly more at 24.

Methods:

Cell Culture Conditions: The Raji and Daudi cell lines were purchased from American Type Culture Collection, were thawed, and grown in RPMI 1640 medium supplemented with standard supplements, including 10% fetal calf serum, gentamycin, penicillin, streptomycin, sodium pyruvate, HEPES buffer, 1-glutamine, and 2-ME.

Protocol: Cells were plated into a 12 well plate with 3 mls total volume containing approximately $1.5 \times 10^6$/well for Daudi cells and $3.0 \times 10^6$/well for Raji cells. Treatment groups included no treatment as control and biotinylated FRIMV-LAS (SEQ ID NO. 2) (also referred to as MKN 5) at 50 microMolar final concentration based on the reported molarity of the synthesized compounds.

The cells were incubated at 37° C. in an atmosphere containing 5% CO2 and approximately 92% humidity. The cells were incubated for 4 and 24 hours. At each time point, the cells from that experimental time were harvested and stained for flow cytometric analysis of cell surface expression of CD1d by staining with PE anti-human CD1d (eBioscience, clone 51.5, cat. #12-00016-71).

Harvested cells were stained using standard staining procedure that called for a 1:100 dilution of PE anti-CD1d. Following staining on ice for 25 minutes, cells were washed with PBS/FCS and resuspended in 100 microliters and added to staining tubes containing 400 microliters of PBS. Samples were acquired and analyzed on a Coulter Excel Flow Cytometer.

Example 10

Preparation of a prodrug ester of this invention can be exemplified by the following Examples.

[3,4,6-trihydroxytetrahydro-2H-pyran-2-yl]methyl dichloroacetate can be prepared by mixing 2-deoxy-D-glucose, dichloroacetate, and sulfuric acid and refluxing the solution. After cooling the solution, one can then add water and diethyl ether for mixing and allow the aqueous and organic layers to separate in order to remove the aqueous layer. The product can then be extracted using sodium bicarbonate until a neutral pH is acquired and then dried over anhydrous sodium sulfate. The diethyl ether will be evaporated over a warm sand bath and the product will be allowed to cool to room temperature.

[3,4,6-trihydroxytetrahydro-2H-pyran-2-yl]methyl dichloroacetate can be prepared by mixing 2-deoxy-D-glucose, anhydrous dichloroacetate, and acetic anhydride and then stirring and refluxing the solution. After the reflux, the contents can be mixed with ice and cold water, then suction filtered and recrystallized in ethanol.

The Mechanism for Acid-Catalyzed Esterification:

The mechanism for the Acid-Catalyzed Esterification of Dichloroacetic Acid is as follows, with R=Halogen, R'=the remainder of 2-deoxy-D-glucose, or an analog or homolog thereof.

Overall Reaction:

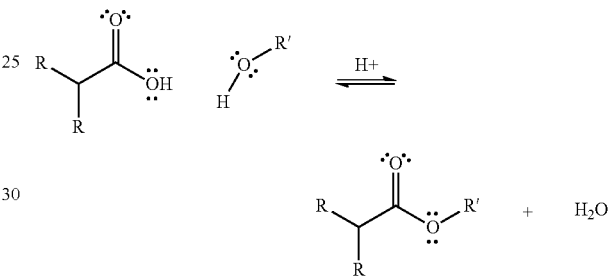

Step 1: The carboxylic acid is protonated on its carbonyl oxygen.

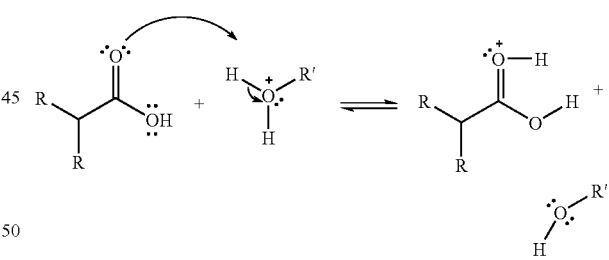

Step 2: Protonation of the carboxylic acid increases the positive character of its carbonyl group. A molecule of the alcohol acts as a nucleophile and attacks the carbonyl carbon.

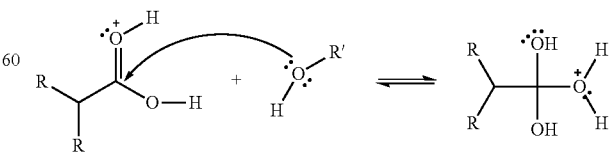

Step 3: the oxonium ion formed in step 2 loses a proton to give the tetrahedral intermediate in its neutral form.

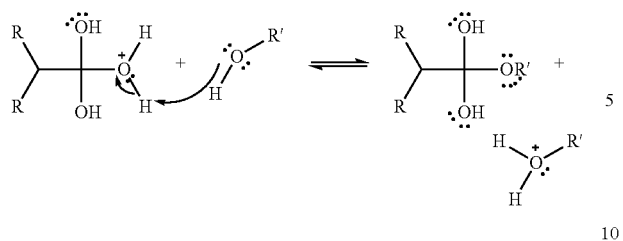

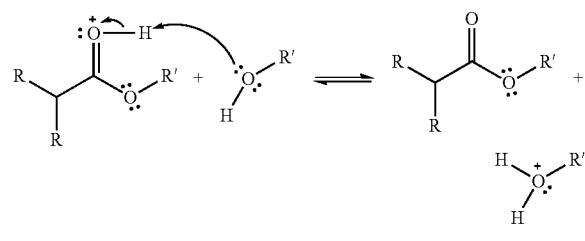

Step 4: The tetrahedral intermediate is hydroxylated.

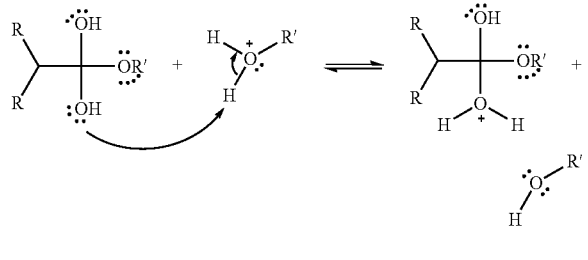

Step 5: The intermediate loses a molecule of water to give the protonated form of the ester.

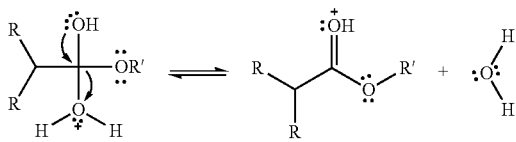

Step 6: Deprotonation of the species formed in step 5 gives the neutral form of the ester product.

REFERENCES

The following references, to the extent that they provide exemplary procedural or other details supplementary to those set forth herein, are specifically incorporated herein by reference.

Cohen et al., *Cancer Res.,* 54:1055, 1994.
Ehlers and Ravitch, *Trends Immunol.,* February 2007.
Goodman and Gilman's *The Pharmacological Basis Of Therapeutics,* Calabresi and Chabner (Eds.), In: *Antineoplastic Agents,* Chapter 52 and Intro, 1202-1263, 8th Ed., McGraw-Hill, Inc., 1990.
Huber et al., *J. Virology,* 73(7):5630-5636, 1999.
Human Mycoses, Beneke (Ed.), Upjohn Co., Kalamazoo, Mich., 1979.
Matza et al., *Trends Immunol.,* 24(5): 264-268, 2003.
Opportunistic Mycoses of Man and Other Animals, Smith (Ed.), CAB Intl., Wallingford, UK, 1989.
Piessens, In: *Scientific American Medicine,* Scientific American Books, 2:1-13, 1996.
Remington's Pharmaceutical Sciences, 18th Ed. Mack Printing Co., 1289-1329, 1990.
Scrip's Antifungal Report, PJB Publications Ltd, 1992.
Stumptner-Cuvelette et al., *Proc. Natl. Acad. Sci. USA,* 98:12144-12149, 2001.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for treating HIV infection comprising: contacting a CLIP molecule expressing cell with an inhibitor of γδT cell expansion, activation and/or effector function in an effective amount to treat the HIV infection, wherein the inhibitor of δγT cell expansion, activation and/or effector function is a CLIP activity inhibitor, wherein the CLIP activity inhibitor is a peptide that displaces CLIP, wherein the agent that displaces CLIP is FRIMAVLAS (SEQ ID NO. 2).

2. The method of claim 1, wherein the CLIP molecule is CLIP.

3. The method of claim 1, further comprising exposing the CLIP molecule expressing cell to an anti-MHC class II antibody.

4. A method for treating a subject infected with HIV comprising: administering to the subject a CLIP inhibitor in an effective amount to reduce CLIP function in a CLIP molecule expressing cell of the subject wherein the CLIP inhibitor is FRIMAVLAS (SEQ ID NO. 2).

5. The method of claim 4, further comprising administering to the subject an anti-MHC class II antibody.

6. The method of claim 4, further comprising administering to the subject a treatment for HIV infection.

7. The method of claim 4, wherein the treatment for HIV infection is a protease inhibitor.

* * * * *

UNITED STATES PATENT AND TRADEMARK OFFICE
CERTIFICATE OF CORRECTION

| | | |
|---|---|---|
| PATENT NO. | : 8,557,764 B2 | Page 1 of 3 |
| APPLICATION NO. | : 12/011643 | |
| DATED | : October 15, 2013 | |
| INVENTOR(S) | : Martha Karen Newell et al. | |

It is certified that error appears in the above-identified patent and that said Letters Patent is hereby corrected as shown below:

IN THE DRAWINGS:

Sheet 7/8, Fig. 4 should be replaced by the attached Fig. 4 as shown on page 2

Sheet 8/8, Fig. 5 should be replaced by the attached Fig. 5 as shown on page 3

Signed and Sealed this
Twentieth Day of May, 2014

Michelle K. Lee
*Deputy Director of the United States Patent and Trademark Office*